US009920071B2

(12) United States Patent
Ueda

(10) Patent No.: US 9,920,071 B2
(45) Date of Patent: Mar. 20, 2018

(54) METHOD FOR PRODUCING INHIBITOR OF ACTIVATED BLOOD COAGULATION FACTOR X (FXA)

(71) Applicant: Daiichi Sankyo Company, Limited, Chuo-ku, Tokyo (JP)

(72) Inventor: Tsuyoshi Ueda, Sagamihara (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 0 days.

(21) Appl. No.: 15/118,903

(22) PCT Filed: Feb. 13, 2015

(86) PCT No.: PCT/JP2015/054001
§ 371 (c)(1),
(2) Date: Aug. 15, 2016

(87) PCT Pub. No.: WO2015/125710
PCT Pub. Date: Aug. 27, 2015

(65) Prior Publication Data
US 2017/0050983 A1 Feb. 23, 2017

(30) Foreign Application Priority Data
Feb. 18, 2014 (JP) ................................ 2014-028266

(51) Int. Cl.
*C07D 513/04* (2006.01)
*A61K 31/444* (2006.01)

(52) U.S. Cl.
CPC .......... *C07D 513/04* (2013.01); *A61K 31/444* (2013.01)

(58) Field of Classification Search
CPC .................................................... C07D 513/04
See application file for complete search history.

(56) References Cited

U.S. PATENT DOCUMENTS

| | | | | |
|---|---|---|---|---|
| 8,058,440 | B2 | 11/2011 | Nagasawa et al. | |
| 8,357,808 | B2 * | 1/2013 | Koyama | C07D 513/04 546/304 |
| 9,233,980 | B2 * | 1/2016 | Kawanami | C07C 201/12 |

FOREIGN PATENT DOCUMENTS

| | | | | |
|---|---|---|---|---|
| EP | 1 270 557 | A1 | 1/2003 | |
| EP | 1 405 852 | A1 | 4/2004 | |
| EP | 1 415 992 | A1 | 5/2004 | |
| EP | 1 577 301 | A1 | 9/2005 | |
| EP | 1 925 611 | A1 | 5/2008 | |
| JP | 2003-183286 | A | 7/2003 | |
| JP | 2013-514325 | A | 4/2013 | |
| WO | 01/74774 | A1 | 10/2001 | |
| WO | 2003/000680 | A1 | 1/2003 | |
| WO | 2003/016302 | A1 | 2/2003 | |
| WO | 2004/058715 | A1 | 7/2004 | |
| WO | 2005/047296 | A1 | 5/2005 | |
| WO | 2007/032498 | A1 | 3/2007 | |
| WO | 2011/073339 | A1 | 6/2011 | |
| WO | WO 2011073339 | A1 * | 6/2011 | C07D 513/04 |
| WO | WO 2012017932 | A1 * | 2/2012 | C07C 201/12 |
| WO | WO 2012031024 | A1 * | 3/2012 | C07D 471/04 |

OTHER PUBLICATIONS

Mori "VI.2.1.1.1 Palladium-Catalyzed Carbonylation of Aryl and Vinylic Halides" Handbook of Organopalladium Chemistry for Organic Synthesis, Edited by Ei-ichi Negishi, 2002 John Wiley & Sons, Inc.*
Cacchi "Palladium-Catalyzed Hydroxycarbonylation of Aryl and Vinyl Halides or Triflates by Acetic Anhydride and Formate Anions." Organic Letters, 2003, 5(23), 4269-4272.*
Fujihara "Palladium-catalyzed esterification of aryl halides using aryl formates without the use of external carbon monoxide." Chemical Communications 2012, 48(64), 8012-8014.*
Ueda "Palladium-Catalyzed Carbonylation of Aryl, Alkenyl, and Allyl Halides with Phenyl Formate." Organic Letters, 2012, 14(12), 3100-3103.*
Labinger "Tutorial on Oxidative Addition" Organometallics 2015, 34, 4784-4795.*
Barnard "Palladium-Catalyzed Carbonylations A Reaction Come of Age" Organometallics 2008, 27, 5402-5422.*
Hansch "A Survey of Hammett Substituent Constants and Resonance and Field Parameters" Chem. Rev. 1991, 91, 165-195.*
International Search Report dated Apr. 14, 2015, issued in corresponding International Application No. PCT/JP2015/054001, filed Feb. 13, 2015, 5 pages.
STN International Registry File, CAS Registration No. 1250410-35-5, "Thiazolo[5,4-c]pyridine-2-carboxylic acid, 4,5,6,7-tetrahydro-5-methyl-,ethyl ester," entered Nov. 1, 2010, SR Chemical Catalog, Supplier: Ukrorgsyntez Ltd., 1 page.
Extended European Search Report dated Jul. 28, 2017, issued in European Application No. EP 15 75 2746, filed Feb. 23, 2015, 6 pages.
Yoshino, T., et al., "Preparation of Ethylenediamine and 1,2-cycloalkanediamine Derivatives as Inhibitors of Activated Blood Coagulation Factor X," Daiichi Pharmaceutical Co., Ltd., Japan; and Chemical Abstracts Service, Columbus, Ohio, Accession No. 135:303902 (abstract) and WO 01/74774, Daiichi Pharmaceutical Co., Ltd., Japan, Oct. 11, 2001.

* cited by examiner

*Primary Examiner* — David K O'Dell
(74) *Attorney, Agent, or Firm* — Christensen O'Connor Johnson Kindness PLLC

(57) ABSTRACT

An object of the present invention is to provide a novel method for producing a compound, a salt thereof, or a hydrate of the compound or the salt, which is an FXa inhibitor. The object can be attained by a production method in which a production method via a compound represented by formula (1-1), etc., from a compound represented by the following formula (1-x), etc., is used for a method for producing a compound represented by the following formula (X), etc. [wherein X represents a halogen atom or the like, and $R^1$ represents an optionally substituted phenyl group].

13 Claims, No Drawings

METHOD FOR PRODUCING INHIBITOR OF ACTIVATED BLOOD COAGULATION FACTOR X (FXA)

TECHNICAL FIELD

The present invention relates to a method for producing compound (X), a pharmacologically acceptable salt thereof, or a hydrate of the compound or the salt, which is an activated blood coagulation factor X (FXa) inhibitor, and a novel industrial method for producing a thiazole derivative, which is an important intermediate for production thereof.

BACKGROUND ART

Compound (X) given below, a pharmacologically acceptable salt thereof, or a hydrate of the compound or the salt, or compound (X-a) given below is, as disclosed in Patent References 1 to 3, a compound that exhibits an FXa inhibitory effect and is useful as a preventive and/or therapeutic drug for thrombotic and/or embolic diseases.

[Formula 1]

(X)

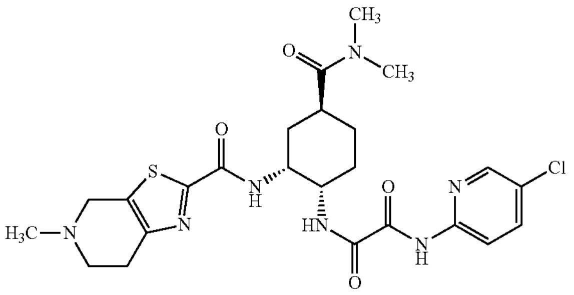

(X-a)

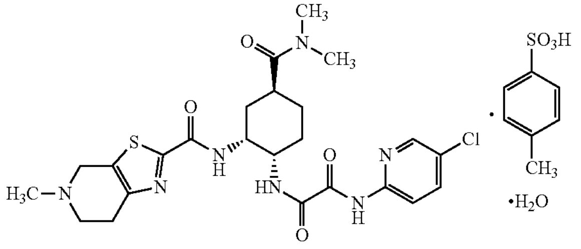

Compound (1-c) given below, which is a thiazole-2-carboxylic acid derivative, and compound (1-c-hcl) given below, which is a hydrochloride thereof, are known as important intermediates for the production of compound (X) and compound (X-a) as shown in the following scheme:

[Formula 2]

(1-c)

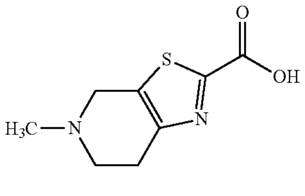

-continued (1-c-hcl)

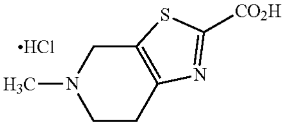

[Formula 3]

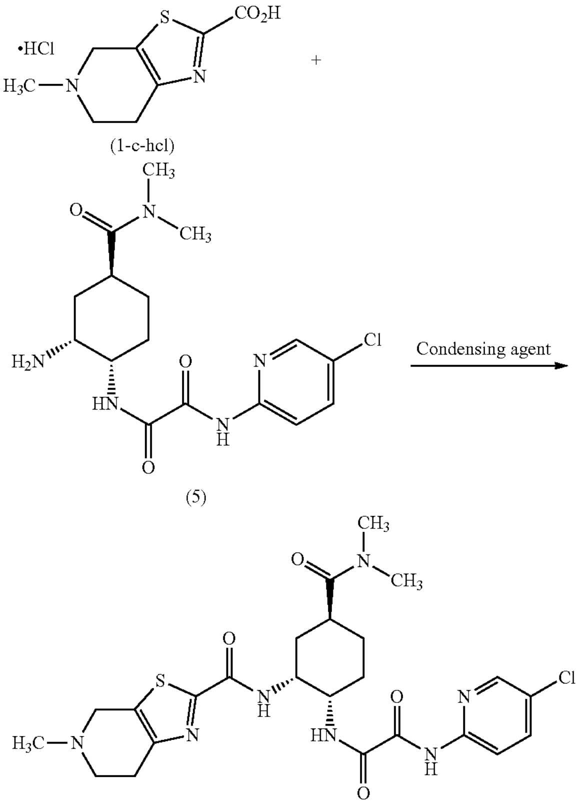

(1-c-hcl)

(5)

(X)

CITATION LIST

Patent References

Patent Reference 1: International Patent Publication No. WO 2004/058715

Patent Reference 2: International Patent Publication No. WO 2003/016302

Patent Reference 3: International Patent Publication No. WO 2003/000680

Patent Reference 4: International Patent Publication No. WO 2005/047296

Patent Reference 5: International Patent Publication No. WO 2007/032498

SUMMARY OF INVENTION

Technical Problem

In the production of FXa inhibitor compound (X) and compound (X-a), the production of compound (1-c-hcl), which is an important intermediate for production, requires production under ultra-low temperature reaction conditions from compound (1-br) as shown in the following scheme:

[Formula 4]

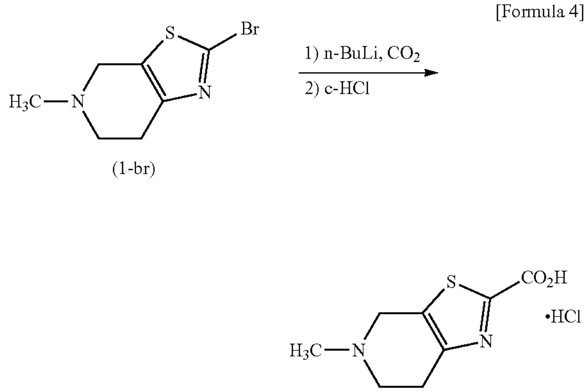

(1-br)

(1-c-hcl)

Also, the production of compound (X) and compound (X-a) from compound (1-c-hcl) requires a condensing agent for the coupling of compound (1-c-hcl) to compound (5), as mentioned above.

Thus, an object of the present invention is to provide a method for producing compound (1-c-hcl), which is an intermediate for the production of compound (X), without the need for ultra-low temperature reaction conditions, and a method for producing compound (X) and compound (X-a) without the need for the condensing agent mentioned above.

Solution to Problem

The present inventors have conducted diligent studies with the aim of attaining the object and completed the present invention by finding that compound (1-x) can be converted to an active ester compound (1-p1) or the like at a high yield through a carbonylation reaction using carbon monoxide or a carbon monoxide substitute in the presence of a reaction catalyst containing a palladium catalyst and a phosphine ligand in combination, and further finding that compound (1-p1) can be subsequently treated with compound (5) in the presence of a phosphoric acid (tri)alkali metal salt to produce compound (X) without the use of a condensing agent.

[Formula 5]

(1-p1)

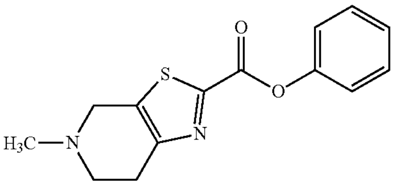

Specifically, the present invention provides the following [1] to [20]:

[1] A method for producing compound (X), a salt thereof, or a hydrate of the compound or the salt:

[Formula 6]

(X)

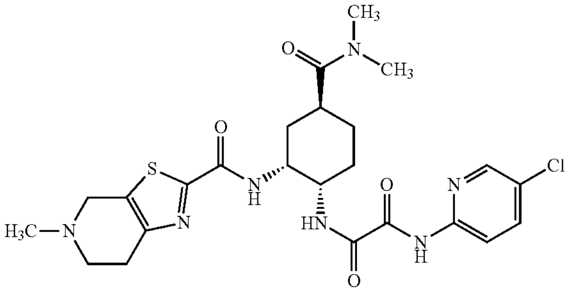

the method comprising:

mixing a compound represented by the following formula (1-x), a salt thereof, or a hydrate of the compound or the salt:

[Formula 7]

(1-x)

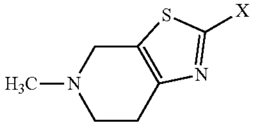

wherein X represents a halogen atom or a —O—$S(O)_2$—$R^0$ group (wherein $R^0$ represents an optionally substituted C1-C6 alkyl group or an optionally substituted phenyl group)

with any of the following (B-1):

(B-1):

(i) a compound represented by formula (3-a): $R^1$—OH (3-a) under a carbon monoxide atmosphere wherein $R^1$ represents an optionally substituted phenyl group, and (ii) a compound represented by formula (4-a): $R^1$—O—CHO (4-a)

wherein $R^1$ is as defined above in the presence of a base and a palladium catalyst (containing a phosphine ligand) in a solvent to produce a compound represented by the following formula (1-1) or a salt thereof:

[Formula 8]

(1-1)

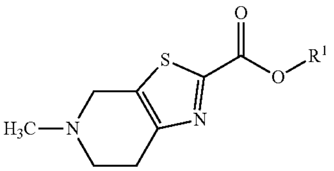

wherein $R^1$ is as defined above; and subsequently mixing the compound represented by formula (1-1) with a compound represented by the following formula (5) or a salt thereof:

[Formula 9]

(5)

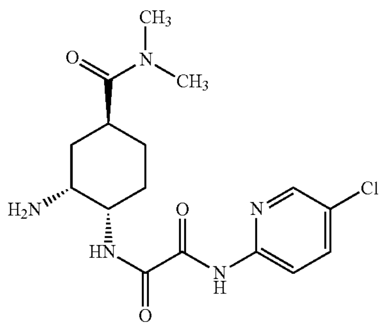

in the presence of a phosphoric acid (tri)alkali metal salt or a carbonic acid alkali metal salt to produce compound (X), a salt thereof, or a hydrate of the compound or the salt.

[2] A method for producing the following compound (X), a salt thereof, or a hydrate of the compound or the salt:

[Formula 10]

(X)

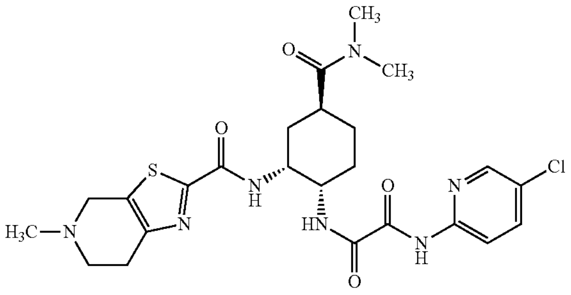

the method comprising:

mixing a compound represented by the following formula (1-x), a salt thereof, or a hydrate of the compound or the salt:

[Formula 11]

(1-x)

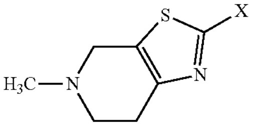

wherein X represents a halogen atom or a —O—S(O)$_2$—R$^0$ group (wherein R$^0$ represents an optionally substituted C1-C6 alkyl group or an optionally substituted phenyl group)

with the following compound (5) or a salt thereof:

[Formula 12]

(5)

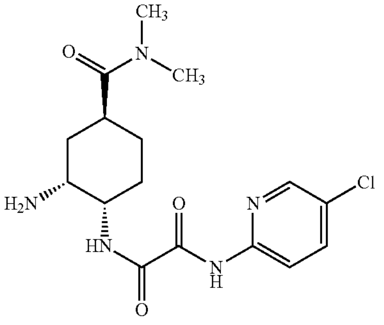

in the presence of a base and a palladium catalyst (containing a phosphine ligand) in a solvent under a carbon monoxide atmosphere to produce compound (X), a salt thereof, or a hydrate of the compound or the salt.

[3] A method for producing the following compound (X), a salt thereof, or a hydrate of the compound or the salt:

[Formula 13]

(X)

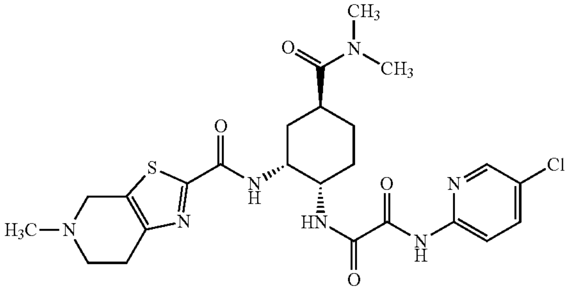

the method comprising:

mixing a compound represented by the following formula (1-x), a salt thereof, or a hydrate of the compound or the salt:

[Formula 14]

(1-x)

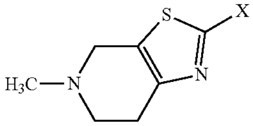

wherein X represents a halogen atom or a —O—S(O)$_2$—R$^0$ group (wherein R$^0$ represents an optionally substituted C1-C6 alkyl group or an optionally substituted phenyl group)

with any of the following (B-2):

(B-2):

(i) a compound represented by formula (3-b): R$^3$—OH (3-b) under a carbon monoxide atmosphere wherein $R^3$ represents a C1-C6 alkyl group or an optionally substituted phenyl group and (ii) a compound represented by formula (4-b): $R^3$—O—CHO (4-b)

wherein $R^3$ represents an optionally substituted phenyl group in the presence of a base and a palladium catalyst (containing a phosphine ligand) in a solvent to produce a compound represented by the following formula (1-3) or a salt thereof:

[Formula 15]

(1-3)

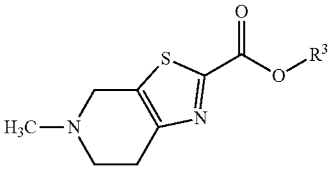

wherein $R^3$ represents a C1-C6 alkyl group or an optionally substituted phenyl group;

subsequently alkali-hydrolyzing the compound represented by formula (1-3) to produce compound (1-c) or a salt thereof:

[Formula 16]

(1-c)

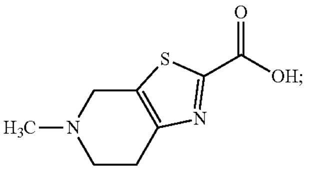

and subsequently mixing the compound represented by formula (1-c) with compound (5) or a salt thereof:

[Formula 17]

(5)

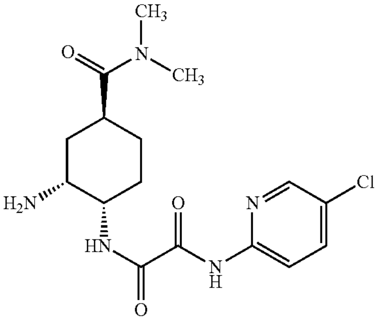

in the presence of a base and a condensing agent to produce compound (X), a salt thereof, or a hydrate of the compound or the salt.

[4] A method for producing compound (X), a salt thereof, or a hydrate of the compound or the salt:

[Formula 18]

(X)

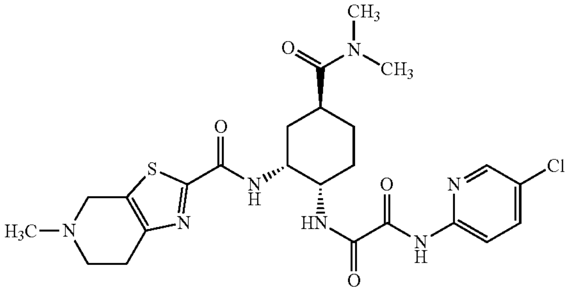

the method comprising:

mixing a compound represented by the following formula (1-x), a salt thereof, or a hydrate of the compound or the salt:

[Formula 19]

(1-x)

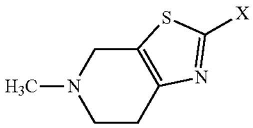

wherein X represents a halogen atom or a —O—$S(O)_2$—$R^0$ group (wherein $R^0$ represents an optionally substituted C1-C6 alkyl group or an optionally substituted phenyl group)

in the presence of a base, acetic anhydride, formic acid or a derivative thereof, and a palladium catalyst (containing a phosphine ligand) in a solvent to produce compound (1-c) or a salt thereof:

[Formula 20]

(1-c)

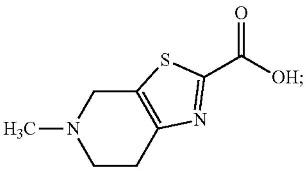

and subsequently mixing the compound (1-c) or the salt thereof with a compound represented by the following formula (5) or a salt thereof:

[Formula 21]

(5)

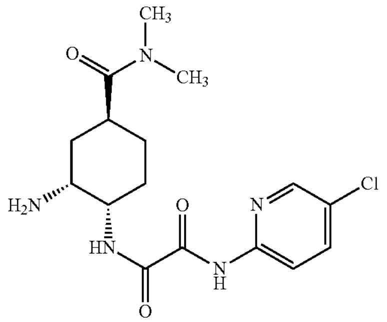

in the presence of a tertiary amine and a condensing agent to produce compound (X), a salt thereof, or a hydrate of the compound or the salt.

[5] A production method according to [4], wherein the formic acid or derivative thereof is potassium formate or sodium formate.

[6] A production method according to any one of [1] to [5], wherein the palladium catalyst (containing a phosphine ligand) contains palladium(II) acetate.

[7] A production method according to any one of [1] to [6], wherein the phosphine ligand in the palladium catalyst (containing a phosphine ligand) is 4,5-bis(diphenylphosphino)-9,9-dimethylxanthene (xantphos).

[8] A production method according to any one of [1] to [7], wherein the base is a tertiary amine, an alkali metal carbonate, or a phosphoric acid alkali metal salt.

[9] A production method according to [8], wherein the tertiary amine is a tri(C1-C4 alkyl) amine, diisopropylethylamine, 1-methylpyrrolidine, 1-methylpiperidine, 4-methylmorpholine, 4 (N,N-dimethylamino)pyridine, pyridine, lutidine, or collidine.

[10] A production method according to any one of [1] to [9], wherein the solvent is a C1-C3 alkane nitrile solvent, an ether solvent, a C1-C6 saturated hydrocarbon solvent, an aromatic hydrocarbon solvent, an amide solvent, a sulfoxide solvent, a phenol solvent (the benzene ring of the phenol optionally has, as substituent(s), 1 to 3 groups selected from the group consisting of a C1-C6 alkyl group, a nitro group, and a halogen atom), or an alcohol solvent.

[11] A production method according to any one of [1] to [10], wherein the compound (X) is a p-toluenesulfonic acid monohydrate of the compound (X) represented by the following compound (X-a):

[Formula 22]

(X-a)

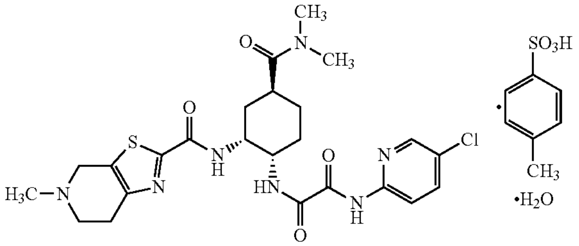

[12] A method comprising mixing a compound represented by the following formula (1-br), a salt thereof, or a hydrate of the compound or the salt:

[Formula 23]

(1-br)

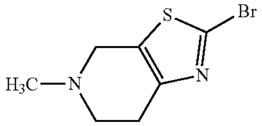

with any of the following (B-3):

(B-3)

(i) a C1-C6 alcohol, phenol, or 2,4,6-trichlorophenol under a carbon monoxide atmosphere, and (ii) phenyl formate or (2,4,6-trichlorophenyl) formate in the presence of a base and a palladium catalyst (containing a phosphine ligand) in a solvent to produce a compound represented by the following formula (1-3) or a salt thereof:

[Formula 24]

(1-3)

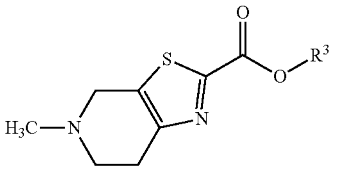

wherein $R^3$ represents a C1-C6 alkyl group, a phenyl group, or a 2,4,6-trichlorophenyl group.

[13] A method comprising mixing a compound represented by the following formula (1-br), a salt thereof, or a hydrate of the compound or the salt:

[Formula 25]

(1-br)

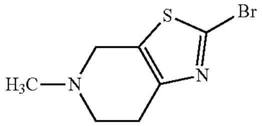

in the presence of a base, acetic anhydride, formic acid or a derivative thereof, and a palladium catalyst (containing a phosphine ligand) in a solvent to produce a compound represented by the following formula (1-c) or a salt thereof:

[Formula 26]

(1-c)

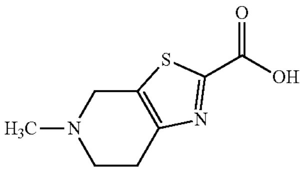

[14] A production method according to [12] or [13], wherein the palladium catalyst (containing a phosphine ligand) contains palladium(II) acetate.

[15] A production method according to any one of [12] to [14], wherein the phosphine ligand in the palladium catalyst (containing a phosphine ligand) is 4,5-bis(diphenylphosphino)-9,9-dimethylxanthene (xantphos).

[16] A production method according to any one of 15 [12] to [15], wherein the base is a tertiary amine, an alkali metal carbonate, or a phosphoric acid alkali metal salt.

[17] A production method according to [16], wherein the tertiary amine is a tri(C1-C4 alkyl) amine, diisopropylethylamine, 1-methylpyrrolidine, 1-methylpiperidine, 4-methylmorpholine, 4 (N,N-dimethylamino)pyridine, pyridine, lutidine, or collidine.

[18] A production method according to any one of [12] to [17], wherein the solvent is a C1-C3 alkane nitrile solvent, an ether solvent, a C1-C6 saturated hydrocarbon solvent, an aromatic hydrocarbon solvent, an amide solvent, a phenol solvent (the benzene ring of the phenol optionally has, as substituent(s), 1 to 3 groups selected from the group consisting of a C1-C6 alkyl group, a nitro group, and a halogen atom), or an alcohol solvent.

[19] A compound represented by the following formula (1-3) or a salt thereof:

[Formula 27]

(1-3)

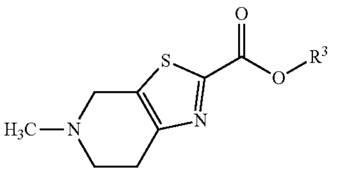

wherein $R^3$ represents a C1-C6 alkyl group or an optionally substituted phenyl group.

[20] A compound according to [19] or a salt thereof, wherein $R^3$ is a phenyl group, a 4-nitrophenyl group, a 4-chlorophenyl group, a 2,4,6-trichlorophenyl group, or a 4-(trifluoromethyl)phenyl group.

Advantageous Effects of Invention

The present invention eliminates the need for ultra-low temperature reaction conditions in the production of compound (1-c-hcl), which is an intermediate for the production of compound (X), and has enabled FXa inhibitor compound (X) and compound (X-a) to be produced easily and at a high yield without the use of a condensing agent. The production method of the present invention is useful as a novel method for producing compound (X).

DESCRIPTION OF EMBODIMENTS

Hereinafter, the present invention will be described in detail.

In the present invention, "halogen atom" means a fluorine atom, a chlorine atom, a bromine atom, and an iodine atom.

In the present invention, "C1-C6 alkyl group" means a monovalent group consisting of a linear or branched saturated hydrocarbon having 1 to 6 carbon atoms. Examples thereof can include a methyl group, an ethyl group, a propyl group, an isopropyl group, a n-butyl group, an isobutyl group, a tert-butyl group, a n-pentyl group, and a n-hexyl group.

In the present invention, "optionally substituted C1-C6 alkyl group" means a C1-C6 alkyl group in which a hydrogen atom may be replaced with a group selected from the group consisting of a C1-C6 alkyl group, a halo-C1-C6 alkyl group, a nitro group, a phenyl group, and a halogen atom. Preferred examples thereof can include a methyl group, an ethyl group, and a trifluoromethyl group.

In the present invention, "optionally substituted phenyl group" means a phenyl group in which 1 to 5 hydrogen atoms in the benzene ring may be replaced with group(s) selected from the group consisting of a C1-C6 alkyl group, a halo-C1-C6 alkyl group, a nitro group, a phenyl group, and a halogen atom. Preferred examples thereof can include a phenyl group, a 4-nitrophenyl group, a 4-chlorophenyl group, a 4-(trifluoromethyl)phenyl group, and a 2,4,6-trichlorophenyl group.

In the present invention, "phenol" means phenol in which 1 to 5 hydrogen atoms in the benzene ring may be replaced with group(s) selected from the group consisting of a C1-C6 alkyl group, a halo-C1-C6 alkyl group, a nitro group, a phenyl group, and a halogen atom. Preferred examples of the phenol according to the present invention can include phenol, 4-nitrophenol, 4-chlorophenol, 4-(trifluoromethyl)phenol, and 2,4,6-trichlorophenol.

In the present invention, "phenol solvent" means phenol optionally having, as substituent(s), 1 to 3 groups selected from the group consisting of a C1-C6 alkyl group, a nitro group, and a halogen atom.

One aspect of the present invention provides a method for producing compound (1-1) from compound (1-x) as shown in the following Scheme A:

Scheme A

[Formula 28]

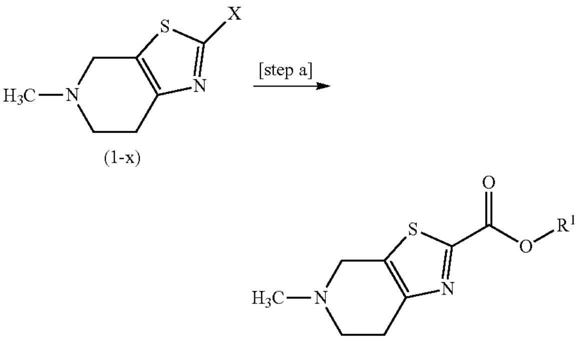

(1-x)

(1-1)

wherein

X represents a halogen atom or a —O—$S(O)_2$—$R^0$ group (wherein $R^0$ represents an optionally substituted C1-C6 alkyl group or an optionally substituted phenyl group); and $R^1$ represents an optionally substituted phenyl group.

A compound represented by compound (1-x), a salt thereof, or a hydrate of the compound or the salt is mixed with any of the following (B-1):

(B-1):

(i) a compound represented by formula (3-a): $R^1$—OH (3-a) under a carbon monoxide atmosphere wherein $R^1$ represents an optionally substituted phenyl group and (ii) a compound represented by formula (4-a): $R^1$—O—CHO (4-a)

wherein $R^1$ is as defined above in the presence of a base and a palladium catalyst (containing a phosphine ligand) in a solvent to produce compound (1-1).

X is more preferably a halogen atom, particularly preferably a bromine atom.

A —O—$S(O)_2$—$R^0$ group means an (optionally substituted C1-C6 alkyl)-sulfonyloxy group or an (optionally substituted phenyl)-sulfonyloxy group and specifically means a leaving group such as a methanesulfonyloxy group, an ethanesulfonyloxy group, a trifluoromethanesulfonyloxy group, a benzenesulfonyloxy group, or a p-toluenesulfonyloxy group.

$R^1$ is preferably a phenyl group or a 2,4,6-trichlorophenyl group.

Examples of the palladium catalyst include palladium(II) acetate ($Pd(OAc)_2$), palladium(II) acetylacetonate, palladium(II) trifluoroacetate, palladium(II) dichloride, tris(dibenzylideneacetone)dipalladium(0), and bis(dibenzylideneacetone)palladium(0). $Pd(OAc)_2$ is particularly preferred.

Examples of the phosphine ligand used at the same time with the palladium catalyst can include 4,5-bis(diphenylphosphino)-9,9-dimethylxanthene (xantphos), 1,1'-bis(diphenylphosphino)ferrocene (dppf), 2,2'-bis(diphenylphosphino)-1,1'-binaphthyl (BINAP), bis(diphenylphosphino) methane (DPPM), triphenylphosphine, tri-o-tolylphosphine, tri-p-tolylphosphine, tricyclohexylphosphine, tributylphosphine, tri-tert-butylphosphine, di(1-adamantyl)-n-butylphosphine, 1,2-bis(diphenylphosphino)ethane (DPPE), 1,3-bis(diphenylphosphino)propane (DPPP), 1,4-bis (diphenylphosphino)butane (DPPB), 1,2-bis (dicyclohexylphosphino)ethane (DCyPE), 1,3-bis (dicyclohexylphosphino)propane (DCyPP), 1,4-bis (dicyclohexylphosphino)butane (DCyPB), 1,2-bisdiphenylphosphinobenzene (DPPBz), bis[2-(diphenylphosphino)phenyl] ether (DPEphos), and 1,1'-bis (di-tert-butylphosphino)ferrocene (Dt-BPF). 4,5-Bis (diphenylphosphino)-9,9-dimethylxanthene (xantphos) is particularly preferred.

The palladium catalyst and the phosphine ligand in catalytic amounts can allow the reaction to proceed. The amounts of the palladium catalyst and the phosphine ligand used are preferably 0.05 to 10% by mol and 0.1 to 20% by mol, respectively, more preferably 0.1 to 5% by mol and 0.2 to 10% by mol, respectively, with respect to 1 mol of the substrate compound (1-x). The ratio between the palladium catalyst and the phosphine ligand used is preferably of the order of palladium catalyst:phosphine ligand=1:2 to 1:4.

In (B-1), (i) compound $R^1$—OH (3-a) under a carbon monoxide atmosphere means that phenol or 2,4,6-trichlorophenol, which is a particularly preferred compound as compound (3-a), is added to a reaction mixture containing compound (1-x), etc., and further, the inside of the reaction system is treated under a carbon monoxide atmosphere.

The amount of phenol or 2,4,6-trichlorophenol added can be equimolar (1 mol) with respect to 1 mol of the substrate compound (1-x). Preferably, phenol or 2,4,6-trichlorophenol is added at approximately 1.5 to approximately 3 mol with respect to 1 mol of the substrate compound (1-x).

In (B-1), (ii) $R^1$—O—CHO (4-a):

compound (4-a) is preferably phenyl formate or (2,4,6-trichlorophenyl) formate in which $R^1$ is a phenyl group or a 2,4,6-trichlorophenyl group.

Examples of the solvent used in [step a] can include:

C1-C3 alkane nitrile solvents such as acetonitrile;

ether solvents such as diethyl ether, 1,2-dimethoxyethane, and tetrahydrofuran;

C1-C6 saturated hydrocarbon solvents such as hexane and pentane;

aromatic hydrocarbon solvents such as benzene, toluene, and chlorobenzene;

amide solvents such as N,N-dimethylformamide, N,N-dimethylacetamide, and 1-methyl-2-pyrrolidone; and sulfoxide solvents such as dimethyl sulfoxide. Alternatively, the phenol used in (i) of (B-1) may be used as a solvent.

The base used in [step a] is preferably:

a tri(C1-C4 alkyl)amine such as triethylamine;

a tertiary amine such as diisopropylethylamine, 1-methylpyrrolidine, 1-methylpiperidine, or 4-methylmorpholine;

pyridine or a derivative thereof such as 4-(N,N-dimethylamino)pyridine, pyridine, lutidine, or collidine;

an alkali metal carbonate such as sodium carbonate, sodium bicarbonate, potassium carbonate, or cesium carbonate; or a phosphoric acid alkali metal salt such as (tri)potassium phosphate, (tri)sodium phosphate, (di)potassium hydrogen phosphate, or (di)sodium hydrogen phosphate, more preferably a tertiary amine.

In this context, since a base is used in this reaction, the substrate compound (1-x) may be an acid-addition salt. The base can be used in an amount supplemented with an amount necessary for the neutralization of the acid-addition salt of compound (1-x). The amount of the base used in this reaction is preferably 1 to 10 mol with respect to 1 mol of compound (1-x).

The reaction temperature of [step a]

can adopt the range of room temperature to the boiling point of the solvent and is preferably room temperature to approximately 100° C., more preferably 40 to 80° C. The reaction time is usually of the order of 2 to 50 hours.

The present invention provides a method for producing compound (X), a salt thereof, or a hydrate of the compound or the salt from compound (1-1) and compound (5) as shown in the following Scheme B:

Scheme B

[Formula 29]

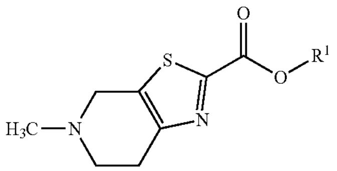

(1-1)

+

-continued

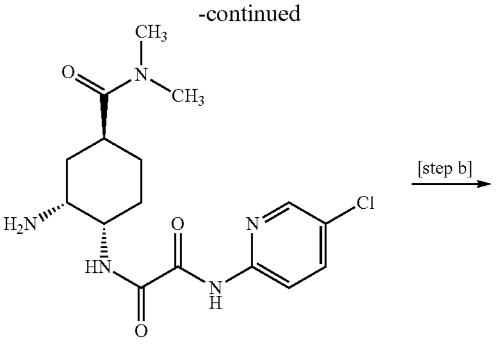

(5)

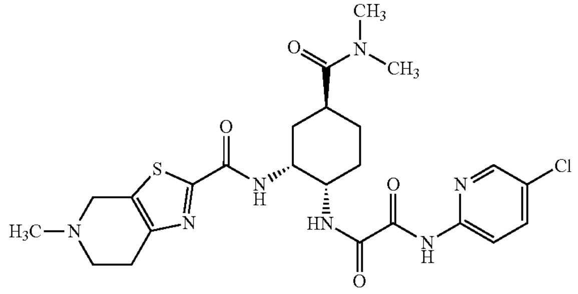

(X)

wherein $R^1$ represents an optionally substituted phenyl group.

In [step b], compound (1-1) and compound (5) or a salt thereof are treated with a phosphoric acid (tri)alkali metal salt or a carbonic acid alkali metal salt to produce compound (X), a salt thereof, or a hydrate of the compound or the salt.

In [step b], an organic solvent is preferably used. The organic solvent is preferably an amide solvent such as N,N-dimethylformamide, N,N-dimethylacetamide, or 1-methyl-2-pyrrolidone.

The phosphoric acid (tri)alkali metal salt or the carbonic acid alkali metal salt used in [step b] is preferably (tri) sodium phosphate, (tri)potassium phosphate, potassium carbonate, or cesium carbonate.

Compound (5) may be used as an acid-addition salt in this reaction. In this case, the amount of the phosphoric acid (tri)alkali metal salt or the carbonic acid alkali metal salt added can be increased.

The amount of the phosphoric acid (tri)alkali metal salt used in [step b] is preferably of the order of 1 to 10 mol, more preferably of the order of 2 to 5 mol, with respect to 1 mol of compound (1-1).

An alternative aspect of the present invention provides a method for producing compound (X), a salt thereof, or a hydrate of the compound or the salt by one step from compound (1-x) and compound (5) or a salt thereof as shown in the following Scheme C:

Scheme C

[Formula 30]

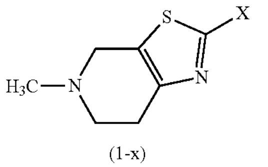

\+

(1-x)

-continued

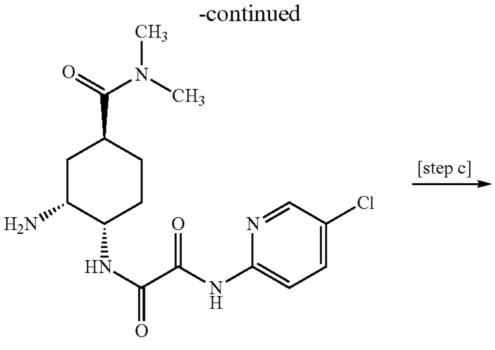

(5)

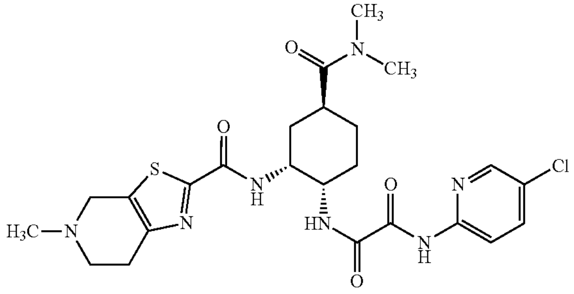

(X)

wherein X represents a halogen atom or a —O—$S(O)_2$—$R^0$ group (wherein $R^0$ represents an optionally substituted C1-C6 alkyl group or an optionally substituted phenyl group)

In this context, X in compound (1-x) is preferably a bromine atom.

In [step c], compound (1-x), a salt thereof, or a hydrate of the compound or the salt is mixed with compound (5) or a salt thereof in the presence of a base and a palladium catalyst (containing a phosphine ligand) under a carbon monoxide atmosphere to produce compound (X), a salt thereof, or a hydrate of the compound or the salt.

In this context, the palladium catalyst is preferably $Pd(OAc)_2$, and the phosphine ligand used at the same time with the palladium catalyst is preferably xantphos.

The amounts of the palladium catalyst and the phosphine ligand used are preferably 0.05 to 10% by mol and 0.1 to 20% by mol, respectively, more preferably 0.1 to 5% by mol and 0.2 to 10% by mol, respectively, with respect to 1 mol of the substrate compound (1-x).

The ratio between the palladium catalyst and the phosphine ligand used is preferably of the order of palladium catalyst:phosphine ligand=1:2 to 1:4.

The reaction under a carbon monoxide atmosphere is preferably carried out using, for example, a balloon filled with carbon monoxide gas.

Examples of the solvent used in this reaction can include the solvent used in [step a] described above. An amide solvent such as N,N-dimethylformamide, N,N-dimethylacetamide, or 1-methyl-2-pyrrolidone is particularly preferred.

As the base used in this reaction, the base used in [step a] described above can be used, and a tertiary amine is preferred. The tertiary amine is preferably: a tri(C1-C4 alkyl)amine such as triethylamine; diisopropylethylamine, 1-methylpyrrolidine, 1-methylpiperidine, 4-methylmorpholine, or the like; or pyridine or a derivative thereof such as 4-(N,N-dimethylamino)pyridine, pyridine, lutidine, or collidine. The amount of the base used is preferably 1 to 10 mol with respect to 1 mol of compound (1-x).

The reaction temperature of this reaction can adopt the range of room temperature to the boiling point of the solvent and is preferably 40 to 80° C. The reaction time is usually of the order of 2 to 50 hours for completion.

Compound (X) produced by the step described above can be treated with commercially available p-toluenesulfonic acid monohydrate in aqueous ethanol to produce compound (X-a).

A further alternative aspect of the present invention provides a method for producing compound (1-c) known in the art, a salt thereof, or a hydrate of the compound or the salt according to the following Scheme D:

Scheme D

[Formula 31]

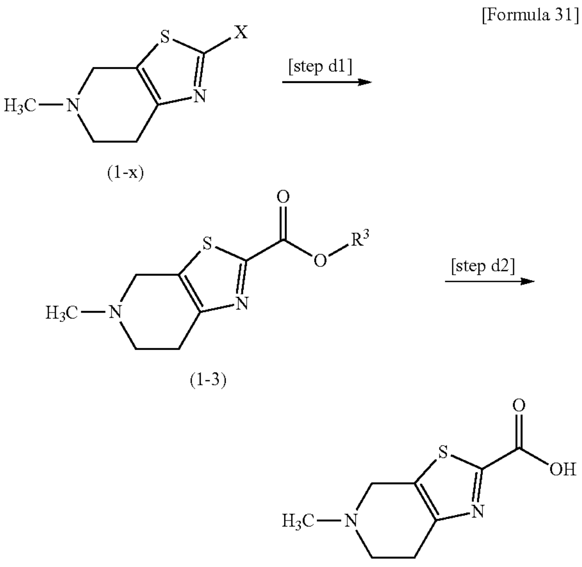

(1-x)

(1-3)

(1-c)

wherein

X represents a halogen atom or a —O—$S(O)_2$—$R^0$ group (wherein $R^0$ represents an optionally substituted C1-C6 alkyl group or an optionally substituted phenyl group); and $R^3$ represents a C1-C6 alkyl group or an optionally substituted phenyl group.

Compound (1-x), a salt thereof, or a hydrate of the compound or the salt is mixed with any of the following (B-2):

(B-2):

(i) a compound represented by the following formula (3-b) under a carbon monoxide atmosphere:

$R^3$—OH (3-b)

wherein $R^3$ represents a C1-C6 alkyl group or an optionally substituted phenyl group, and (ii) a compound represented by the following formula (4-b):

$R^3$—O—CHO (4-b)

wherein $R^3$ represents an optionally substituted phenyl group in the presence of a base and a palladium catalyst (containing a phosphine ligand) in a solvent to produce compound (1-c).

X is particularly preferably a bromine atom.

$R^3$ in compounds (3-b) and (4-b) is preferably a phenyl group and a 2,4,6-trichlorophenyl group.

$R^3$ in compound (3-b) is also preferably a methyl group, an ethyl group, a n-propyl group, an isopropyl group, a n-butyl group, a tert-butyl group, a phenyl group, or a 2,4,6-trichlorophenyl group.

Specifically, compound (3-b) is preferably methanol, ethanol, n-propanol, isopropanol, n-butanol, tert-butanol, phenol, or 2,4,6-trichlorophenol.

The palladium catalyst is more preferably $Pd(OAc)_2$.

The phosphine ligand used at the same time with the palladium catalyst is preferably xantphos.

The amounts of the palladium catalyst and the phosphine ligand used are preferably 0.05 to 10% by mol and 0.1 to 20% by mol, respectively, more preferably 0.1 to 5% by mol and 0.2 to 10% by mol, respectively, with respect to 1 mol of the substrate compound (1-x). The ratio between the palladium catalyst and the phosphine ligand used is preferably of the order of palladium catalyst:phosphine ligand=1:2.

In (B-2), (i) $R^3$—OH (3-b) and (ii) $R^3$—O—CHO (4-b) are specifically as described below.

(i) The reaction is carried out under a carbon monoxide atmosphere in a reaction system supplemented with a C1-C6 alcohol, phenol, or 2,4,6-trichlorophenol.

The amount of C1-C6 alcohol, phenol, or 2,4,6-trichlorophenol added can be equimolar (1 mol) with respect to 1 mol of the substrate compound (1-x). Preferably, the C1-C6 alcohol, phenol, or 2,4,6-trichlorophenol is added at approximately 1.5 to approximately 3 mol with respect to 1 mol of the substrate compound (1-x).

(ii) $R^3$—O—CHO (4-b) has been reported to serve as a carbon monoxide substitute in the literature (Organic Letters 2012 14 5370). In the present invention, compound (4) is preferably phenyl formate or (2,4,6-trichlorophenyl) formate in which $R^3$ is a phenyl group or a 2,4,6-trichlorophenyl group.

Examples of the reaction solvent used in [step d1] can include:

C1-C3 alkane nitrile solvents such as acetonitrile;

ether solvents such as diethyl ether, 1,2-dimethoxyethane, and tetrahydrofuran;

C1-C6 saturated hydrocarbon solvents such as hexane and pentane;

aromatic hydrocarbon solvents such as benzene, toluene, and chlorobenzene;

amide solvents such as N,N-dimethylformamide, N,N-dimethylacetamide, and 1-methyl-2-pyrrolidone; and sulfoxide solvents such as dimethyl sulfoxide. Alternatively, a C1-C6 alcohol or phenol or the like used in (i) may be used as a solvent.

The base used in [step d1] is preferably a tertiary amine.

The tertiary amine is preferably: a tri(C1-C4 alkyl)amine such as triethylamine; diisopropylethylamine, 1-methylpyrrolidine, 1-methylpiperidine, 4-methylmorpholine, or the like; or pyridine or a derivative thereof such as 4-(N,N-dimethylamino)pyridine, pyridine, lutidine, or collidine.

Since a base is used in [step d1], the substrate compound (1-x) may be an acid-addition salt. The base can be used in an amount supplemented with an amount necessary for the neutralization of the acid-addition salt of compound (1-x). The amount of the tertiary amine used in this reaction is preferably 1 to 10 mol with respect to 1 mol of compound (1-x).

The reaction temperature of this reaction can adopt the range of room temperature to the boiling point of the solvent and is preferably room temperature to approximately 100° C., more preferably 40 to 80° C. The reaction time is usually of the order of 2 to 50 hours for completion.

[Step d2] is a step of hydrolyzing compound (1-3), which is a C1-C6 alkyl ester or phenyl ester, to produce compound (1-c).

The hydrolysis is preferably alkali hydrolysis and is preferably carried out using an alkali metal hydroxide such as sodium hydroxide, potassium hydroxide, or lithium hydroxide, particularly preferably lithium hydroxide.

After the completion of hydrolysis, compound (1-3) is preferably converted to a compound represented by the following formula (1-c-hcl) by treatment with hydrochloric acid:

[Formula 32]

(1-c-hcl)

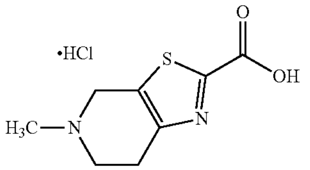

Furthermore, compound (1-c) can also be produced in one step by hydrolysis without isolating compound (1-3), as shown in Scheme F given below.

Compound (1-c) or a salt thereof is subjected to a condensation reaction known in the art with compound (5), a salt thereof, or a hydrate of the compound or the salt to produce compound (X), a salt thereof, or a hydrate of the compound or the salt as shown in the following Scheme F:

Scheme F

[Formula 33]

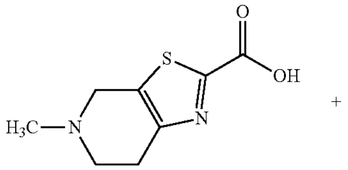

(1-c)

-continued

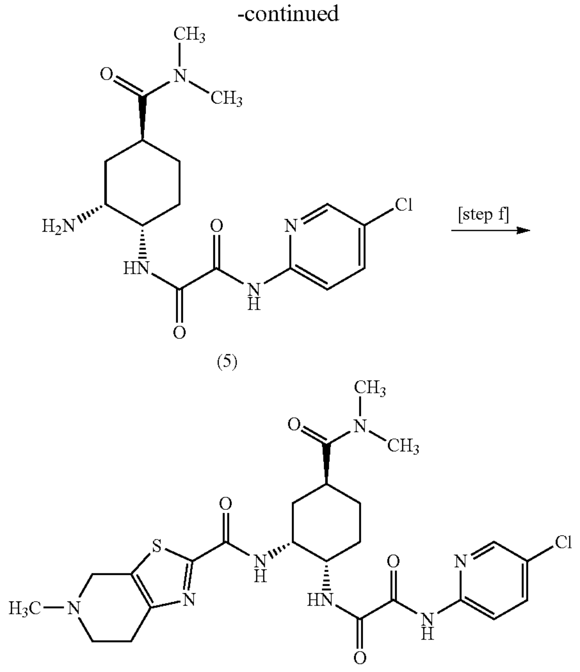

(5)

(X)

For example, a method described in International Patent Publication No. WO 2007/032498 can be applied to [step f]. Compound (1-c), a salt thereof, or a hydrate of the compound or the salt, and compound (5), a salt thereof, or a hydrate of the compound or the salt are treated with, for example, 1-ethyl-3-(3-dimethylaminopropyl)carbodiimide hydrochloride as a condensing agent by using, for example, acetonitrile as a solvent in the presence of a tertiary amine such as triethylamine to produce compound (X). Also, 1-hydroxybenzotriazole may be added as a reaction accelerator during the reaction. In this context, compound (X) thus produced can be treated with commercially available p-toluenesulfonic acid monohydrate in aqueous ethanol to produce compound (X-a).

The present invention further provides a production method shown in the following Scheme G:

Scheme G

[Formula 34]

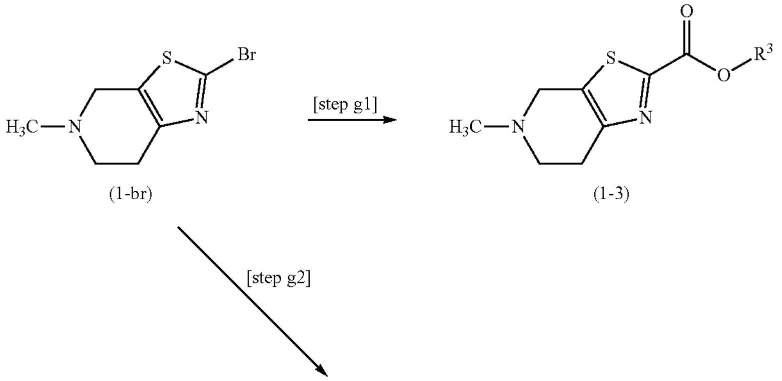

(1-br)

(1-3)

-continued

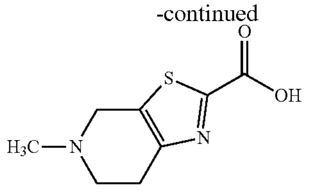

(1-c)

wherein $R^3$ represents a C1-C6 alkyl group, a phenyl group, or a 2,4,6-trichlorophenyl group.

[Step g1] is a method of treating compound (1-br) with any of the following (B-3):

(B-3):

(i) a C1-C6 alcohol, phenol, or 2,4,6-trichlorophenol under a carbon monoxide atmosphere, and (ii) phenyl formate or (2,4,6-trichlorophenyl) formate in the presence of a base and a palladium catalyst (containing a phosphine ligand) in a solvent to produce compound (1-3).

As for the base and the (A) palladium catalyst (containing a phosphine ligand) in a solvent in [step g1], the palladium catalyst is preferably $Pd(OAc)_2$, and the phosphine ligand is preferably xantphos, as with [step d1] described above.

The amounts of the palladium catalyst and the phosphine ligand used are preferably 0.1 to 5% by mol and 0.2 to 10% by mol, respectively, with respect to 1 mol of the substrate compound (1-br). The ratio between the palladium catalyst and the phosphine ligand used is preferably of the order of palladium catalyst:phosphine ligand=1:2.

The reaction solvent in [step g1] is preferably: a C1-C3 alkane nitrile solvent such as acetonitrile; or an aromatic hydrocarbon solvent such as benzene, toluene, or chlorobenzene.

The base used in [step g1] is the same as that in [step a] described above and is preferably a tertiary amine. The tertiary amine is preferably: a tri(C1-C4 alkyl)amine such as triethylamine; diisopropylethylamine, 1-methylpyrrolidine, 1-methylpiperidine, 4-methylmorpholine, or the like; or pyridine or a derivative thereof such as 4 (N,N-dimethylamino)pyridine, pyridine, lutidine, or collidine.

Since compound (1-br) is used as a starting material in [step g1], the amount of the tertiary amine used is preferably 2 to 10 mol with respect to 1 mol of compound (1-br).

[Step g2] is a method of mixing compound (1-br) with a tertiary amine, acetic anhydride, formic acid or a derivative thereof, and a palladium catalyst (containing a phosphine ligand) in a solvent to produce compound (1-c).

Those described in [step e] can be applied to the reagents, the amounts of the reagents, and the solvent used in [step g2]. Formic acid or a derivative thereof means formic acid, a formic acid alkali metal salt, or ammonium formate. A formic acid alkali metal salt is preferred.

The formic acid alkali metal salt is preferably sodium formate or potassium formate. The palladium catalyst is preferably $Pd(OAc)_2$. The phosphine ligand is preferably xantphos.

The amounts of the palladium catalyst and the phosphine ligand used are more preferably 0.1 to 5% by mol and 0.2 to 10% by mol, respectively, with respect to 1 mol of the substrate compound (1-br). The ratio between the palladium catalyst and the phosphine ligand used is preferably of the order of palladium catalyst:phosphine ligand=1:2.

Compound (1-c) is preferably converted to hydrochloride compound (1-c-hcl) by treatment with hydrochloric acid.

EXAMPLES

Next, the present invention will be described in detail with reference to the Examples. However, the present invention is not limited by these Examples by any means.

Tetramethylsilane was used as the internal standard for the nuclear magnetic resonance (NMR) spectra. Abbreviations showing multiplicity are s=singlet, d=doublet, t=triplet, q=quartet, m=multiplet, and brs=broad singlet.

The abbreviations listed below were used.

2-PrOH: 2-propanol
MeOH: methanol
$Et_3N$: triethylamine
MeCN: acetonitrile
DMF: N,N-dimethylformamide
DME: dimethoxyethane
IPA: isopropyl alcohol
$Pd(OAc)_2$: palladium(II) acetate
Xantphos: 4,5-bis(diphenylphosphino)-9,9-dimethylxanthene
NaOH: sodium hydroxide
HCl: hydrochloric acid
HCOOK: potassium formate
$Ac_2O$: acetic anhydride
DIPEA: diisopropylethylamine
THF: tetrahydrofuran
LiOH: lithium hydroxide
$H_2O$: water
$K_3PO_4$: tripotassium phosphate
IPE: isopropyl ether <Analysis Conditions Used in HPLC>

HPLC Analysis Conditions [1]

Column: YMC Pack Pro C18 4.6×100 (3 μm)
Mobile phase: MeCN:10 mM $NH_4OAc$ aq.=20:80-80:20
Temperature: 40° C., Flow rate: 1 mL/min, Detection wavelength: 210 nm
Gradient conditions: 0-5 min: MeCN 20%, 5-15 min: MeCN 20→80%, 15-22 min: MeCN 80%
Retention time: TPCA-ME 4.4 min, TPB 8.8 min, TPCA-PE 13.9 min HPLC Analysis Conditions [2]

Column: Inertsil ODS-3 4.6×250 (5 μm)
Mobile phase: MeCN:phosphate buffer solution (pH 7)=20:80 (10 mM dodecyltrimethyl ammonium chloride)
Temperature: 40° C., Flow rate: 1 mL/min, Detection wavelength: 210 nm
Retention time: TPCA 14.0 min, TPB 16.7 min HPLC Analysis Conditions [3]

Column: YMC Pack Pro C18 4.6×100 (3 μm)
Mobile phase: MeCN:10 mM $NH_4OAc$ aq.=20:80-90:10

Temperature: 40° C., Flow rate: 1 mL/min, Detection wavelength: 210 nm

Gradient conditions: 0-5 min: MeCN 20%, 5-20 min: MeCN 20→90%, 20-25 min: MeCN 90%

Retention time: TPB 7.0 min, DU-176 14.0 min (Reference Example 1) 2-Amino-5-methyl-4,5,6,7-tetrahydrothiazolo[5,4-c]pyridine (1-n) (method described in International Patent Publication No. WO 2005/047296)

[Formula 35]

(1-n)

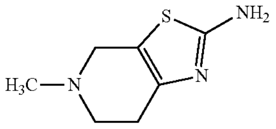

To a solution of 1-methyl-4-piperidone (180.0 g) in 2-PrOH (1.44 L) heated to 50° C., a solution of cyanamide (67.0 g) in 2-PrOH (360 mL), and a sulfur powder (51.0 g) were added. To the reaction mixture, pyrrolidine (13.3 mL) was added, and the mixture was stirred at 50° C. for 2 hours, then left to cool to room temperature, and stirred overnight.

The reaction mixture was cooled to 10° C. or lower in an ice water bath and stirred at the same temperature as above for 1 hour. The deposited crystals were filtered, washed with 2-PrOH (540 mL), and then dried under reduced pressure at 40° C. to obtain the title compound (209.9 g, 78%).

$^1$H-NMR ($CDCl_3$) δ ppm: 4.86 (br, 2H), 3.47-3.46 (t, 2H, J=1.9 Hz), 2.78-2.71 (m, 2H), 2.71-2.65 (m, 2H), 2.47 (s, 3H).

MS(FAB) m/z: 170 $(M+H)^+$

Elemental analysis: as $C_7H_{11}N_3S$

Calcd: C, 49.68; H, 6.55; N, 24.83; S, 18.95.

Found: C, 49.70; H, 6.39; N, 24.91; S, 19.00.

(Reference Example 2) 2-Amino-5-methyl-4,5,6,7-tetrahydrothiazolo[5,4-c]pyridine dihydrobromide (1-n-hbr) (method described in International Patent Publication No. WO 2005/047296)

[Formula 36]

(1-n-hbr)

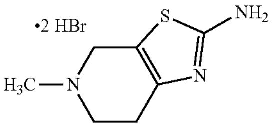

1-Methyl-4-piperidone (100.0 g) was dissolved in 2-PrOH (800 mL) at room temperature. The solution was then heated in a hot water bath to raise the internal temperature to 50° C.

A solution of cyanamide (37.16 g) in 2-PrOH (200 mL), and a sulfur powder (28.34 g) were added thereto at 50° C. A catalytic amount of pyrrolidine (7.4 mL) was further added thereto, and the mixture was stirred at 50 to 64° C. for 1 hour and then brought back to room temperature.

To the reaction solution, 48% hydrobromic acid (358.0 g) was added dropwise at 30 to 40° C. Then, the mixture was cooled to 10° C. or lower in an ice water bath and stirred at the same temperature as above for 1 hour and 30 minutes. The deposited crystals were filtered, washed with 2-PrOH (500 mL), and dried under reduced pressure at 40° C. to obtain the title compound (258.2 g, 88%).

$^1$H-NMR ($D_2O$) δ ppm: 4.45-4.53 (d, 1H, J=15.2 Hz), 4.20-4.26 (d, 1H, J=15.2 Hz), 3.75-3.90 (m, 1H), 3.50-3.67 (m, 1H), 3.10 (s, 3H), 2.91-3.18 (m, 2H).

Elemental analysis: as $C_7H_{13}Br_2N_3S$

Calcd: C, 25.39; H, 3.96; Br, 48.27; N, 12.69; S, 9.69.

Found: C, 25.54; H, 3.93; Br, 48.09; N, 12.62; S, 9.72.

(Reference Example 3) 2-Bromo-5-methyl-4,5,6,7-tetrahydrothiazolo[5,4-c]pyridine (1-br) (method described in International Patent Publication No. WO 2005/047296)

[Formula 37]

(1-br)

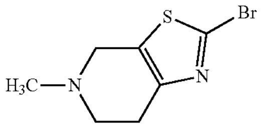

Compound (1-n) (600.0 g) was suspended in water (6.0 L). To the suspension, 48% hydrobromic acid (4.2 L) was then added dropwise at 5 to 15° C.

To the reaction mixture, a solution of sodium nitrite (367.2 g) dissolved in water (1.8 L) was added dropwise at 0 to 5° C. over 1 hour and 30 minutes, and the mixture was then stirred at 30° C. for 24 hours.

The reaction mixture was rendered strongly alkaline (pH: approximately 12.5) by the addition of a 5 N aqueous NaOH solution (6.0 L), and the aqueous layer was then subjected to extraction with toluene twice (12.0 L and 6.0 L). The extracts were dried by the addition of anhydrous sodium sulfate (1202.0 g). Then, insoluble matter was filtered off, and the mother liquor was then concentrated under reduced pressure at 40° C. to obtain the title compound (557.6 g).

$^1$H-NMR ($CDCl_3$) δ ppm: 3.58-3.57 (t, 3H, J=1.8 Hz), 2.92-2.87 (m, 2H), 2.81-2.76 (m, 2H), 2.49 (s, 3H).

(Reference Example 4) 2-Bromo-5-methyl-4,5,6,7-tetrahydrothiazolo[5,4-c]pyridine p-toluenesulfonate (1-br-ts) (method described in International Patent Publication No. WO 2005/047296)

[Formula 38]

(1-br-ts)

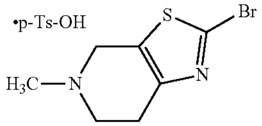

Compound (1-br) (557.6 g) was dissolved in MeOH (3.9 L). To this solution, a solution of commercially available p-toluenesulfonic acid monohydrate (500.0 g) in MeOH (1.7 L) was added dropwise at 30° C., and the mixture was then stirred at the same temperature as above for 1 hour and then at 10° C. or lower for 2 hours. The deposited crystals were filtered, washed with MeOH (1.1 L), and then dried under reduced pressure at 40° C. to obtain the title compound (851.9 g).

$^1$H-NMR (DMSO-$d_6$) δ ppm: 10.15 (br, 1H), 7.47-7.43 (d, 2H, J=8.2 Hz), 7.09-7.07 (d, 2H, J=8.2 Hz), 4.47 (s, 2H), 3.58 (s, 2H), 3.04 (t, 2H, J=6.1 Hz), 2.96 (s, 3H), 2.29 (s, 3H).

Elemental analysis: as $C_{14}H_{17}BrN_2O_3S_2$

Calcd: C, 41.48; H, 4.23; Br, 19.71; N, 6.91; S, 15.82.

Found: C, 41.52; H, 4.33; Br, 19.80; N, 6.99; S, 15.90.

(Reference Example 5) 2-Bromo-5-methyl-4,5,6,7-tetrahydrothiazolo[5,4-c]pyridine p-toluenesulfonate (1-br-ts) (method described in International Patent Publication No. WO 2005/047296)

To a mixed solution of water (250 mL) and 48% hydrobromic acid (175 mL), compound (1-n-hbr) (50.01 g) was added at room temperature and suspended therein. While the internal temperature of this suspension was kept at 10° C. or lower, a solution of sodium nitrite (15.63 g) dissolved in water (75 mL) was added dropwise thereto over 1 hour and 30 minutes.

The reaction mixture was stirred at 10° C. or lower for 20 hours. Then, while the temperature was kept at 20° C. or lower, the reaction mixture was rendered alkaline (pH was 13.1) by the dropwise addition of a 10 N aqueous NaOH solution (175 mL). After extraction with toluene twice (375 mL and 250 mL), ¼ of the volume of the extracts was used in the following operation.

The toluene layer was concentrated under reduced pressure, and the concentrated residue was dissolved by the addition of MeOH (43.8 mL). To this solution, a solution of p-toluenesulfonic acid monohydrate (5.03 g) dissolved in MeOH (18.8 mL) was added dropwise at room temperature. Then, while the temperature was kept at 10° C. or lower, the mixture was stirred for 1 hour and 30 minutes. The deposited crystals were filtered, washed with MeOH (18.8 mL), and then dried under reduced pressure at 40° C. to obtain the title compound (9.05 g).

$^1$H-NMR (DMSO-$d_6$) δ ppm: 10.15 (br, 1H), 7.47-7.43 (d, 2H, J=8.2 Hz), 7.09-7.07 (d, 2H, J=8.2 Hz), 4.47 (s, 2H), 3.58 (s, 2H), 3.04 (t, 2H, J=6.1 Hz), 2.96 (s, 3H), 2.29 (s, 3H).

Elemental analysis: as $C_{14}H_{17}BrN_2O_3S_2$

Calcd: C, 41.48; H, 4.23; Br, 19.71; N, 6.91; S, 15.82.

Found: C, 41.54; H, 4.18; Br, 19.83; N, 7.03; S, 16.02.

(Reference Example 6) 5-Methyl-4,5,6,7-tetrahydrothiazolo[5,4-c]pyridine-2-carboxylic acid hydrochloride (1-c-hcl) (method described in International Patent Publication No. WO 2005/047296)

[Formula 39]

(1-c-hcl)

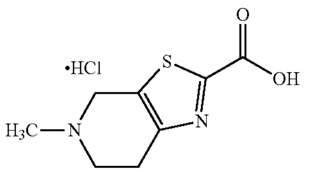

Compound (1-br-ts) (40.00 g) and a 1 N aqueous NaOH solution (200 mL) were mixed at room temperature and stirred for 30 minutes, followed by extraction with toluene twice (400 mL×2). The extracts were washed with 5% saline (200 mL) and then concentrated into 80 mL under reduced pressure at an external temperature of 50° C. or lower (solution weight after concentration: 91.03 g). A sample for moisture content measurement was collected from the concentrate (solution weight after sampling: 87.68 g).

The moisture content of the sampled concentrate was measured using a Karl Fischer moisture titrator and consequently was 0.0231% (weight ratio).

The concentrate after the sampling was dissolved in anhydrous THF (231 mL), and the atmosphere in the flask containing the solution was converted to an argon atmosphere. The solution was cooled to an internal temperature of −30° C. or lower. Then, while the internal temperature was kept at −30° C. or lower, n-butyllithium (1.59 mol/L solution in n-hexane, 61.7 mL) was added dropwise thereto. The mixture was further stirred at the same temperature as above for 1 hour.

While the internal temperature was kept at −30° C. or lower, $CO_2$ was absorbed to the reaction mixture. The reaction mixture was further stirred for 1 hour under a $CO_2$ atmosphere.

The internal temperature was raised to 15° C. Then, the deposited solid was dissolved by the addition of MeOH (193 mL).

While the internal temperature was kept at 20° C. or lower, concentrated hydrochloric acid (19.3 mL) was added dropwise to the reaction mixture.

The mixture was cooled to an internal temperature of 10° C. or lower and then stirred at the same temperature as above for 1 hour. The deposited crystals were filtered, washed with MeOH (58 mL), and then dried under reduced pressure at room temperature to obtain the title compound (21.20 g).

$^1$H-NMR ($D_2O$) δ ppm: 4.82-4.88 (d, 1H, J=16.0 Hz), 4.51-4.57 (d, 1H, J=16.0 Hz), 3.88-3.96 (m, 1H), 3.60-3.70 (m, 1H), 3.22-3.33 (m, 2H), 3.15 (s, 3H).

MS(EI) m/z: 198 $(M)^+$

Elemental analysis: as $C_8H_{11}ClN_2O_2S$

Calcd: C, 40.94; H, 4.72; Cl, 15.11; N, 11.94; S, 13.66.

Found: C, 40.83; H, 4.56; Cl, 14.81; N, 11.91; S, 13.87.

(Reference Example 7) tert-Butyl[(1R,2S,5S)-2-({[(5-chloropyridin-2-yl)amino](oxo)acetyl}amino)-5-(dimethylaminocarbonyl)cyclohexyl]carbamic acid (5-boc) (method described in International Patent Publication No. WO 2007/032498)

[Formula 40]

(5-boc)

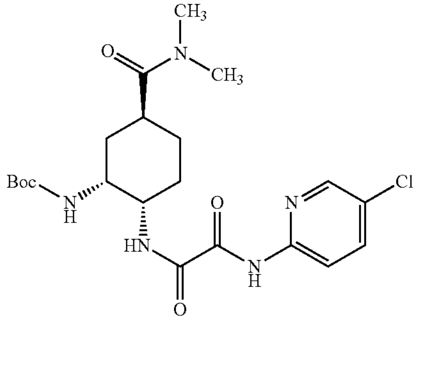

tert-Butyl{(1R,2S,5S)-2-amino-5-[(dimethylamino)carbonyl]cyclohexyl}carbamic acid oxalic acid (100.1 g) was suspended in MeCN (550 mL). To the suspension, $Et_3N$ (169 mL) was added at 60° C. To the mixture, ethyl [5-chloropyridin-2-yl]amino](oxo)acetate hydrochloride (84.2 g) was added at the same temperature as above, and the resulting mixture was stirred for 6 hours.

Then, the reaction mixture was brought back to room temperature and stirred for 16 hours. To the reaction mixture, water was added, and the mixture was stirred at 10° C. for 1.5 hours. The deposited crystals were filtered and dried to obtain 106.6 g of the title compound.

(Reference Example 8) N-(5-Chloropyridin-2-yl)-N'-[(1S,2R,4S)-2-amino-4-(N,N-dimethylcarbamoyl)-cyclohexyl]ethanediamide methanesulfonate (5-ms) (produced with reference to the method described in International Patent Publication No. WO 2007/032498)

[Formula 41]

(5-ms)

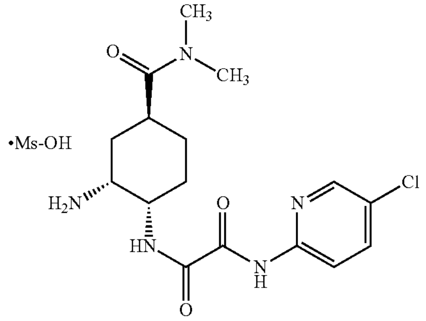

Compound (5-boc) (compound of Reference Example 7) (95.1 g) was suspended in MeCN (1900 mL). To the suspension, methanesulfonic acid (66 mL) was added at room temperature, and the mixture was stirred at the same temperature as above for 2 hours. The reaction solution was concentrated under reduced pressure, and the concentrated residue was used as the title compound.

(Example 1) 5-Methyl-4,5,6,7-tetrahydro[1,3]thiazolo[5,4-c]pyridine-2-carboxylic acid phenyl ester (1-p1)

[Formula 42]

(1-p1)

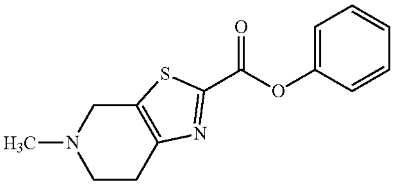

To a 25 mL flask, compound (1-br-ts) (500 mg, 1.234 mmol), $Pd(OAc)_2$ (5.5 mg, 0.025 mmol), and xantphos (28.6 mg, 0.049 mmol) were added.

In a glove box under a current of nitrogen, a solution containing phenol (174 mg, 1.851 mmol) and $Et_3N$ (0.43 mL, 3.085 mmol) in degassed MeCN (5 mL: the degassing was carried out by repeated reduction in pressure and purging with nitrogen three times) was added to the reaction mixture. Reduction in pressure and purging with carbon monoxide (balloon) were repeated three times, and the mixture was stirred at 60° C. for 24 hours under a carbon monoxide atmosphere. The reaction solution obtained was quantitatively analyzed for the production of the title compound (363.3 mg, 94.7%) under HPLC conditions [1].

(Example 2 ) 5-Methyl-4,5,6,7-tetrahydro[1,3]thiazolo[5,4-c]pyridine-2-carboxylic acid methyl ester (1-m)

[Formula 43]

(1-m)

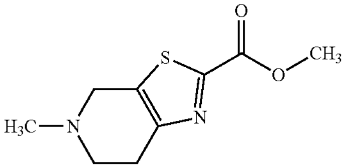

To a 50 mL flask, compound (1-br-ts) (500 mg, 1.234 mmol), $Pd(OAc)_2$ (5.5 mg, 0.025 mmol), and xantphos (28.6 mg, 0.049 mmol) were added. In a glove box under a current of nitrogen, a solution containing $Et_3N$ (0.43 mL, 3.085 mmol) in degassed MeOH (5 mL: the degassing was carried out by repeated reduction in pressure and purging with nitrogen three times) was added to the reaction mixture. Reduction in pressure and purging with carbon monoxide (balloon) were repeated three times, and the mixture was stirred at 60° C. for 26 hours under a carbon monoxide atmosphere. The reaction solution obtained was analyzed and quantified (228.7 mg, 87.3%) under HPLC conditions [1].

After concentration of the reaction solution, chloroform (5 mL) was added to the residue, and the mixture was filtered. After concentration of the filtrate, the residue was purified by thin-layer chromatography ($SiO_2$, EtOAc) to obtain the title compound (171.5 mg, 65.5%).

$^1$H-NMR (500 Hz, $CDCl_3$) δ: 3.99 (s, 3H), 3.74 (t, 2H, J=1.5 Hz), 3.02 (tt, 2H, J=1.5, 6.0 Hz), 2.84 (t, 2H, J=6.0 Hz), 2.52 (s, 3H).

(Example 3) 5-Methyl-4,5,6,7-tetrahydro[1,3]thiazolo[5,4-c]pyridine-2-carboxylic acid phenyl ester (1-p1)

To a 100 mL autoclave, compound (1-br-ts) (5.0 g, 12.34 mmol), $Pd(OAc)_2$ (2.8 mg, 0.0123 mmol), and xantphos (14.3 mg, 0.0247 mmol) were added. In a glove box under a current of nitrogen, a solution containing phenyl formate (2.26 g, 18.50 mmol) and $Et_3N$ (4.3 mL, 30.85 mmol) in degassed MeCN (20 mL: the degassing was carried out by repeated reduction in pressure and purging with nitrogen three times) was added to the reaction mixture. After sealing, the mixture was stirred at 60° C. for 23 hours.

After cooling of the reaction solution, toluene (50 mL) was added thereto, and the mixture was washed with 0.5 M aq. NaOH (50 mL) and 20% saline (25 mL) and concentrated into 10 mL under reduced pressure. To the residue, IPA (50 mL) and c-HCl (1.5 g, 1.2 eq.) were added, and the mixture was concentrated into 20 mL under reduced pressure, followed by the further addition of IPA (10 mL). The slurry obtained was stirred at room temperature for 1 hour and then under ice cooling for 1 hour and filtered. The crystals obtained were washed with IPA (5 mL) of 0 to 5° C. and dried under reduced pressure to obtain the title compound (3.45 g, 89.8%).

$^1$H-NMR (400 Hz, $CDCl_3$) δ: 7.35 (t, 2H, J=8.0 Hz), 7.23-7.17 (m, 3H), 3.71 (s, 2H), 3.01 (t, 2H, J=8.0 Hz), 2.80 (t, 2H, J=8.0 Hz), 2.46 (s, 3H).

(Example 4) 5-Methyl-4,5,6,7-tetrahydro[1,3]thiazolo[5,4-c]pyridine-2-carboxylic acid phenyl ester (1-p1)

In Example 3, phenyl formate (1.5 equivalents) and the catalysts $Pd(OAc)_2$ (0.1 mol %) and xantphos (0.2 mol %) were used with respect to 1 mol of compound (1-br-ts). The same treatment as in Example 3 was carried out for 21 hours except that phenyl formate (2 equivalents), $Pd(OAc)_2$ (0.1 mol %), and xantphos (0.2 mol %) were used. The resultant was quantitatively analyzed for the production of the title compound (98%) under HPLC conditions [1].

(Example 5) 5-Methyl-4,5,6,7-tetrahydro[1,3]thiazolo[5,4-c]pyridine-2-carboyxlic acid 2,4,6-trichlorophenyl ester (1-p2)

[Formula 44]

(1-p2)

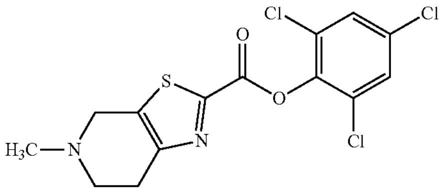

To a 50 mL two-neck eggplant-shaped flask, compound (1-br-ts) (2.0 g, 4.93 mmol), $Pd(OAc)_2$ (33 mg, 0.148 mmol), xantphos (128 mg, 0.222 mmol), and (2,4,6-trichlorophenyl) formate (1.67 g, 7.40 mmol) were added.

After purging with nitrogen, degassed toluene (15 mL: reduction in pressure and purging with nitrogen were repeated three times) was added thereto, and the mixture was heated to 55° C. To the reaction solution, $Et_3N$ (1.6 mL, 2.5 equiv) was added dropwise over 10 minutes (carbon monoxide was generated; use caution not to leak carbon monoxide to the outside of the system)

The reaction solution was stirred at 55° C. for 15 hours, then cooled, and separated into organic and aqueous layers by the addition of $H_2O$ (10 mL), followed by extraction from the aqueous layer with toluene (10 mL) The mixed organic layers were washed with 0.25 M aq. NaOH (20 mL) three times and $H_2O$ (20 mL) in this order, and the solvent was distilled off by concentration under a condition of reduced pressure. To the residue, IPE (20 mL) was added, and the slurry obtained was stirred at room temperature for 1 hour and filtered.

The crystals obtained were dried under reduced pressure to obtain the title compound (1.51 g, 76.8%) (extraction losses in the mother liquor were confirmed to be 16.0% under HPLC analysis conditions [1]).

$^1$H-NMR (500 Hz, $CDCl_3$) δ: 7.42 (s, 2H), 3.80 (s, 2H), 3.10 (t, 2H, J=5.5 Hz), 2.89 (t, 2H, J=5.5 Hz), 2.54 (s, 3H).

(Example 6) 5-Methyl-4,5,6,7-tetrahydro[1,3]thiazolo[5,4-c]pyridine-2-carboxylic acid 2,4,6-trichlorophenyl ester (1-p2)

In Example 5, the catalysts $Pd(OAc)_2$ (3 mol %) and xantphos (4.5 mol %) were used with respect to 1 mol of compound (1-br-ts). The same treatment as in Example 5 was carried out for 24 hours except that $Pd(OAc)_2$ (1.0 mol %) and xantphos (1.5 mol %) were used. The resultant was quantitatively analyzed for the production of the title compound (90%) under HPLC conditions [1].

(Example 7) 5-Methyl-4,5,6,7-tetrahydro[1,3]thiazolo[5,4-c]pyridine-2-carboxylic acid (1-c)

[Formula 45]

(1c)

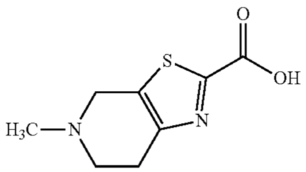

To a 50 mL flask, compound (1-br-ts) (500 mg, 1.234 mmol), HCOOK (512 mg, 3.702 mmol), $Pd(OAc)_2$ (5.5 mg, 0.025 mmol), and xantphos (28.6 mg, 0.049 mmol) were added. In a glove box under a current of nitrogen, a solution containing $Ac_2O$ (128 μL, 1.357 mmol) and DIPEA (0.53 mL, 3.085 mmol) in degassed DME (5 mL: the degassing was carried out by repeated reduction in pressure and purging with nitrogen three times) was added to the reaction mixture, and the mixture was stirred at 60° C. for 24 hours under a nitrogen atmosphere. The title compound in the reaction solution obtained was quantified (199.6 mg, 68.9%) under HPLC conditions [2].

(Example 8) 5-Methyl-4,5,6,7-tetrahydrothiazolo[5,4-c]pyridine-2-carboxylic acid hydrochloride (1-c-hcl)

[Formula 46]

(1d)

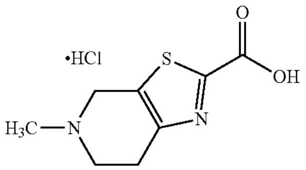

To a 100 mL autoclave, compound (1-br-ts) (5.0 g, 12.34 mmol), $Pd(OAc)_2$ (2.8 mg, 0.0123 mmol), and xantphos (14.3 mg, 0.0247 mmol) were added. In a glove box under a current of nitrogen, a solution containing phenyl formate (2.26 g, 18.50 mmol) and $Et_3N$ (5.1 mL, 36.99 mmol) in degassed MeCN (20 mL: the degassing was carried out by repeated reduction in pressure and purging with nitrogen three times) was added to the reaction mixture. After sealing, the mixture was stirred at 60° C. for 39 hours. After cooling of the reaction solution, toluene (50 mL) was added thereto, and the mixture was washed with 1% NaOH (50 mL) and 20% saline (25 mL) and concentrated into 10 mL under reduced pressure.

To the residue, THF (20 mL), $H_2O$ (2 mL), and $LiOH.H_2O$ (1.04 g, 2.0 equiv) were added, and the mixture was stirred at room temperature for 2 hours. To the reaction solution, c-HCl (3.86 g, 3.5 eq.) and MeOH (50 mL) were added, and the slurry was stirred at room temperature for 1 hour and then under ice cooling for 1 hour and filtered. The crystals obtained were washed with MeOH (10 mL) of 0 to 5° C. and dried under reduced pressure to obtain the title compound (2.51 g, 86.5%) as white crystals.

$^1$H-NMR (500 Hz, DMSO-$d_6$) δ: 4.63-4.55 (m, 2H), 3.62-3.57 (m, 2H), 3.23-3.14 (m, 2H), 2.94 (s, 3H).

(Example 9) $N^1$-(5-Chloropyridin-2-yl)-$N^2$-[(1S,2R,4S)-4-(dimethylcarbamoyl)-2-{[(5-methyl-4,5,6,7-tetrahydro[1,3]thiazolo[5,4-c]pyridin-2-yl)carbonyl]amino}cyclohexyl]ethanediamide (X)

[Formula 47]

(X)

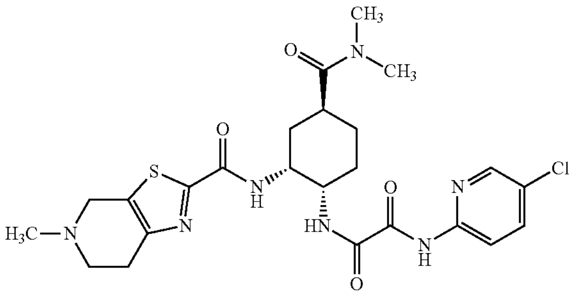

To a 50 mL flask, compound (1-br-ts) (2.0 g, 4.93 mmol), compound (5-ms) (compound of Reference Example 8) (2.52 g, 5.43 mmol), $Pd(OAc)_2$ (33 mg, 0.148 mmol), and xantphos (171 mg, 0.296 mmol) were added. In a glove box under a current of nitrogen, a solution containing $Et_3N$ (2.4 mL, 17.26 mmol) in degassed DMF (20 mL: the degassing was carried out by repeated reduction in pressure and purging with nitrogen three times) was added to the reaction mixture, and reduction in pressure and purging with carbon monoxide were repeated three times for the reaction system. After creation of a carbon monoxide atmosphere, the mixture was stirred at 60° C. for 17 hours. The title compound produced in the reaction solution obtained was quantified (1.37 g, 50.7%) under HPLC conditions [3].

(Example 10) $N^1$-(5-Chloropyridin-2-yl)-$N^2$-[(1S,2R,4S)-4-(dimethylcarbamoyl)-2-{[(5-methyl-4,5,6,7-tetrahydro[1,3]thiazolo[5,4-c]pyridin-2-yl)carbonyl]amino}cyclohexyl]ethanediamide (X) [production method via compound (1-p1)]

To a 50 mL flask, compound (5-ms) (compound of Reference Example 8) (1.0 g, 2.16 mmol), compound (1-p1) (1.18 g, 4.31 mmol), $K_3PO_4$ (1.83 g, 8.64 mmol), and DMF (10 mL) were added, and the mixture was stirred at room temperature for 3 days. To the reaction solution, $H_2O$ (20 mL) was added, and the slurry obtained was stirred at room temperature for 1 hour, then cooled to 0 to 5° C., and further stirred for 1 hour, followed by the filtration of the solid. The solid obtained was washed with $H_2O$ (10 mL) and dried under reduced pressure to obtain the title compound (0.99 g, 83.9%) as a white solid.

(Example 11) $N^1$-(5-Chloropyridin-2-yl)-$N^2$-[(1S,2R,4S)-4-(dimethylcarbamoyl)-2-{[(5-methyl-4,5,6,7-tetrahydro[1,3]thiazolo[5,4-c]pyridin-2-yl)carbonyl]amino}cyclohexyl]ethanediamide (X) [production method via compound (1-p2)]

To a 10 mL test tube, compound (5-ms) (compound of Reference Example 8) (100 mg, 0.216 mmol), compound (1-p2) (81.4 mg, 0.216 mmol), $K_3PO_4$ (91.7 mg, 0.432 mmol), and DMF (1 mL) were added, and the mixture was stirred under a condition of room temperature for 3 hours. To the reaction solution, $H_2O$ (2 mL) was added, and the slurry obtained was stirred overnight at room temperature, followed by the filtration of the solid. The solid obtained was washed with $H_2O$ (1 mL) and dried under reduced pressure to obtain the title compound (110.0 mg, 92.9%) as a solid.

$^1$H-NMR (500 Hz, $CDCl_3$) δ: 9.72 (s, 1H), 8.30 (dd, 1H, J=2.5, 0.5 Hz), 8.17 (dd, 1H, J=9.0, 0.5 Hz), 8.03 (d, 1H, J=8.5 Hz), 7.68 (dd, 1H, J=9.0, 2.5 Hz), 7.39 (d, 1H, J=8.5 Hz), 4.70-4.67 (m, 1H), 4.13-4.09 (m, 1H), 3.73 (d, 1H, J=16.0 Hz), 3.70 (d, 1H, J=16.0 Hz), 3.06 (s, 3H), 2.96-2.93 (m, 2H), 2.95 (s, 3H), 2.89-2.79 (m, 3H), 2.52 (s, 3H), 2.14-2.06 (m, 3H), 1.96-1.90 (m, 1H), 1.84-1.78 (m, 1H), 1.69-1.62 (m, 1H).

The invention claimed is:

1. A method for producing compound (X) or a hydrate of the compound:

(X)

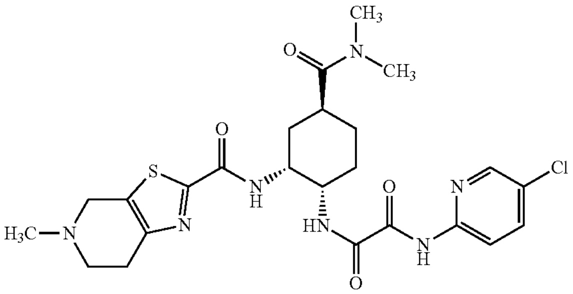

the method comprising:

mixing a compound represented by formula (1-x), a salt thereof, or a hydrate of the compound or the salt:

(1-x)

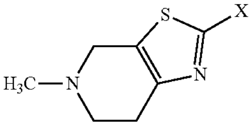

wherein X represents a halogen atom or a —O—S(O)$_2$—$R^0$ group (wherein $R^0$ represents an optionally substituted C1-C6 alkyl group or an optionally substituted phenyl group)

with any of the following:

(i) a compound represented by formula (3-a): $R^1$—OH (3-a) under a carbon monoxide atmosphere wherein $R^1$ represents an optionally substituted phenyl group, and (ii) a compound represented by formula (4-a): $R^1$—O—CHO (4-a)

wherein $R^1$ is as defined above in the presence of a base and a palladium catalyst containing a phosphine ligand in a solvent to produce a compound represented by formula (1-1) or a salt thereof:

(1-1)

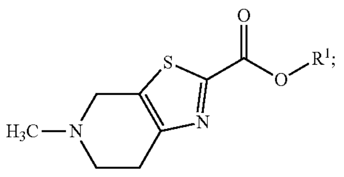

and subsequently mixing the compound represented by formula (1-1) with a compound represented by the following formula (5) or a salt thereof:

(5)

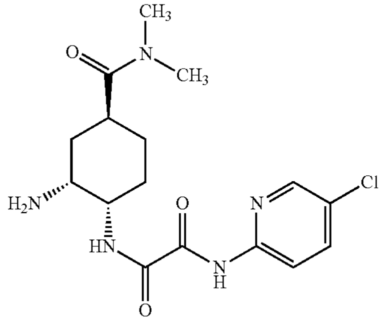

in the presence of a phosphoric acid (tri)alkali metal salt or a carbonic acid alkali metal salt to produce compound (X) or a hydrate of the compound.

2. A method for producing compound (X) or a hydrate of the compound:

(X)

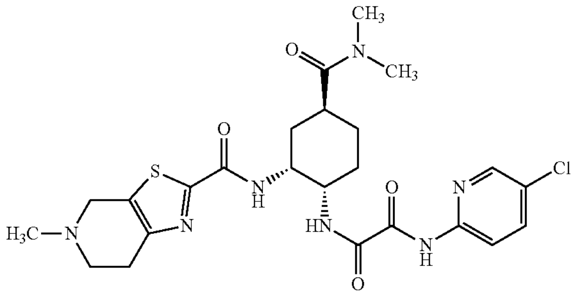

the method comprising:

mixing a compound represented by formula (1-x), a salt thereof, or a hydrate of the compound or the salt:

(1-x)

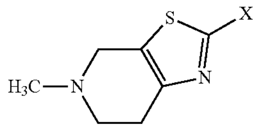

wherein X represents a halogen atom or a —O—S(O)$_2$—$R^0$ group (wherein $R^0$ represents an optionally substituted C1-C6 alkyl group or an optionally substituted phenyl group)

with the following compound (5) or a salt thereof:

(5)

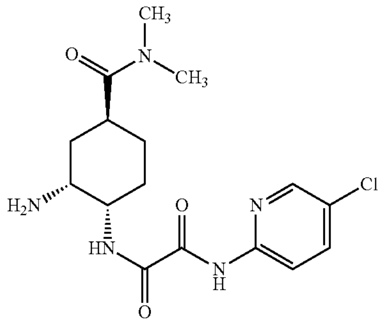

in the presence of a base and a palladium catalyst containing a phosphine ligand in a solvent under a carbon monoxide atmosphere to produce compound (X) or a hydrate of the compound.

3. A method for producing compound (X) or a hydrate of the compound:

(X)

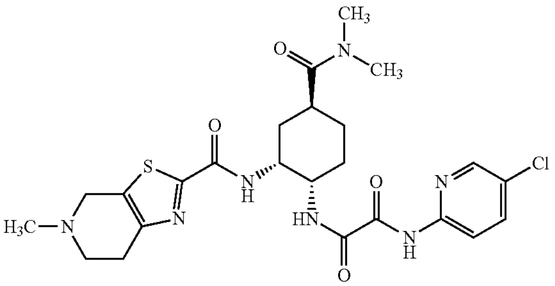

the method comprising:

mixing a compound represented by formula (1-x), a salt thereof, or a hydrate of the compound or the salt:

(1-x)

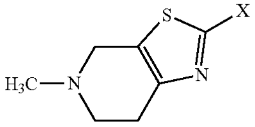

wherein X represents a halogen atom or a —O—S(O)$_2$—$R^0$ group (wherein $R^0$ represents an optionally substituted C1-C6 alkyl group or an optionally substituted phenyl group)

with any of the following:

(i) a compound represented by formula (3-b): $R^3$—OH (3-b) under a carbon monoxide atmosphere wherein $R^3$ represents a C1-C6 alkyl group or an optionally substituted phenyl group, in the presence of a base and palladium (II) acetate catalyst containing 4,5-bis(diphenylphosphino)-9,9-dimethylxanthene (xantphos) phosphine ligand in a solvent, wherein the catalyst is present in the amount 0.1-10 mol %;

or (ii) a compound represented by formula (4-b): $R^3$—O—CHO (4-b)

wherein $R^3$ represents an optionally substituted phenyl group in the presence of a base and a palladium (II) acetate catalyst containing 4,5-bis(diphenylphosphino)-9,9-dimethylxanthene (xantphos) phosphine ligand in a solvent, wherein the catalyst is present in the amount of 0.1-10 mol, to produce a compound represented by formula (1-3) or a salt thereof:

(1-3)

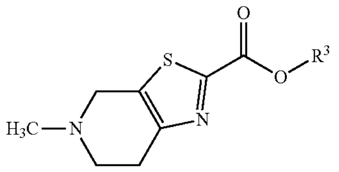

wherein $R^3$ represents a C1-C6 alkyl group or an optionally substituted phenyl group;

subsequently alkali-hydrolyzing the compound represented by formula (1-3) to produce compound (1-c) or a salt thereof:

(1-c)

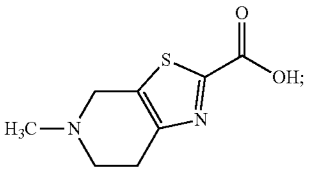

and subsequently mixing the compound represented by formula (1-c) with compound (5) or a salt thereof:

(5)

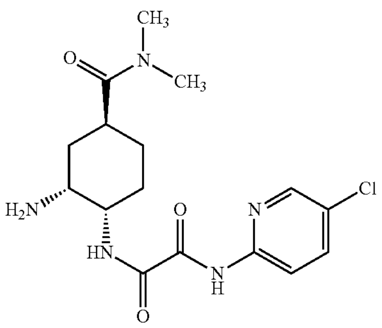

in the presence of a base and a condensing agent to produce compound (X) or a hydrate of the compound.

4. A method for producing compound (X) or a hydrate of the compound:

(X)

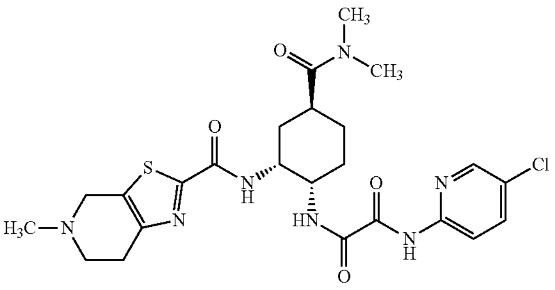

the method comprising:

mixing a compound represented by formula (1-x), a salt thereof, or a hydrate of the compound or the salt:

(1-x)

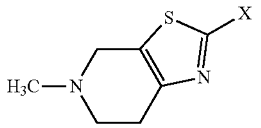

wherein X represents a halogen atom or a —O—$S(O)_2$—$R^0$ group (wherein $R^0$ represents an optionally substituted C1-C6 alkyl group or an optionally substituted phenyl group)

in the presence of a base, acetic anhydride, a formic acid derivative selected from potassium formate or sodium formate, and a palladium catalyst containing a phosphine ligand in a solvent to produce compound (1-c) or a salt thereof:

(1-c)

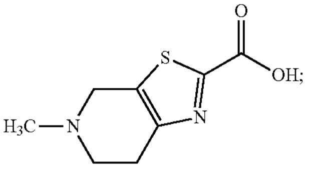

and subsequently mixing the compound (1-c) or the salt thereof with a compound represented by the following formula (5) or a salt thereof:

(5)

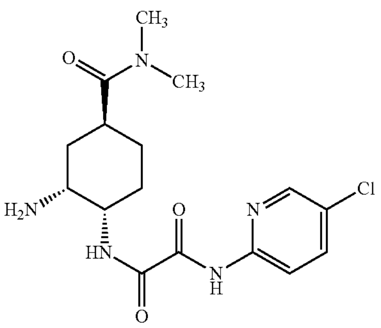

in the presence of a tertiary amine and a condensing agent to produce compound (X) or a hydrate of the compound.

5. A production method according to claim 1, wherein the palladium catalyst containing a phosphine ligand contains palladium(II) acetate.

6. A production method according to claim 1, wherein the phosphine ligand in the palladium catalyst containing a phosphine ligand is 4,5-bis(diphenylphosphino)-9,9-dimethylxanthene (xantphos).

7. A production method according to claim 1, wherein the base is a tertiary amine, an alkali metal carbonate, or a phosphoric acid alkali metal salt.

8. A production method according to claim 7, wherein the tertiary amine is a tri(C1-C4 alkyl) amine, diisopropylethylamine, 1-methylpyrrolidine, 1-methylpiperidine, 4-methylmorpholine, 4-(N,N-dimethylamino)pyridine, pyridine, lutidine, or collidine.

9. A production method according to claim 1, wherein the solvent is a C1-C3 alkane nitrile solvent, an ether solvent, a C1-C6 saturated hydrocarbon solvent, an aromatic hydrocarbon solvent, an amide solvent, a sulfoxide solvent, a phenol solvent (the benzene ring of the phenol optionally has, as substituent(s), 1 to 3 groups selected from the group consisting of a C1-C6 alkyl group, a nitro group, and a halogen atom), or an alcohol solvent.

10. A method for producing a p-toluenesulfonic acid monohydrate of a compound represented by formula (X):

(X)

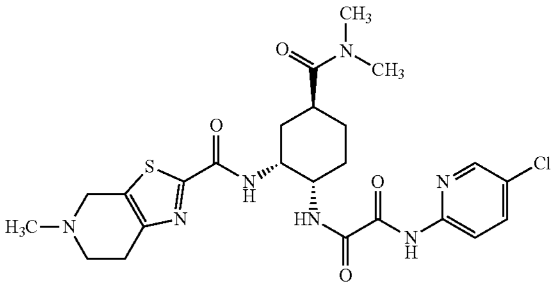

the method comprising:

(a) mixing a compound represented by formula (1-x), a salt thereof, or a hydrate of the compound or the salt:

(1-x)

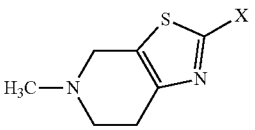

wherein X represents a halogen atom or a —O—$S(O)_2$—$R^0$ group (wherein $R^0$ represents an optionally substituted C1-C6 alkyl group or an optionally substituted phenyl group)

with any of the following (i) a compound represented by formula (3-a): $R^1$—OH (3-a) under a carbon monoxide atmosphere wherein $R^1$ represents an optionally substituted phenyl group, and (ii) a compound represented by formula (4-a): $R^1$—O—CHO (4-a)

wherein $R^1$ is as defined above, in the presence of a base and a palladium catalyst containing a phosphine ligand in a solvent to produce a compound represented by formula (1-1) or a salt thereof:

(1-1)

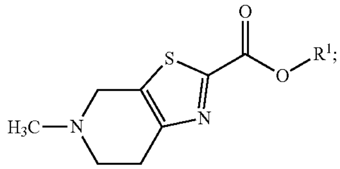

(b) mixing the compound represented by formula (1-1) with a compound represented by formula (5) or a salt thereof:

(5)

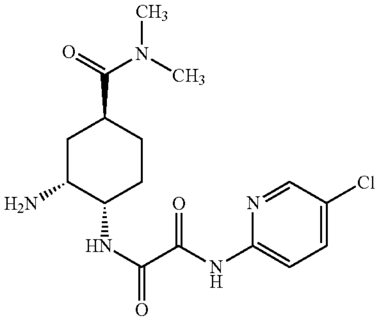

in the presence of a phosphoric acid (tri)alkali metal salt or a carbonic acid alkali metal salt to produce compound (X); and (c) treating compound (X) with p-toluenesulfonic acid monohydrate in aqueous ethanol to provide the p-toluenesulfonic acid monohydrate of compound (X) represented by formula (X-a):

(X-a)

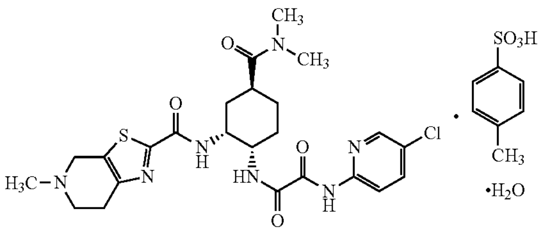

.

11. A method for producing a p-toluenesulfonic acid monohydrate of a compound represented by formula (X):

(X)

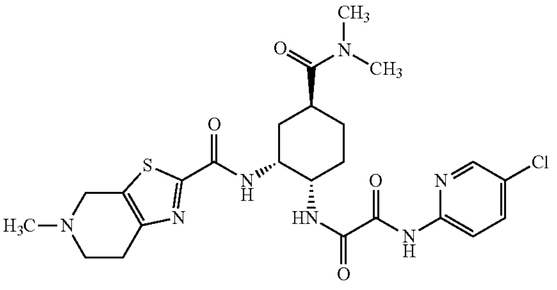

the method comprising:

(a) mixing a compound represented by formula (1-x), a salt thereof, or a hydrate of the compound or the salt:

(1-x)

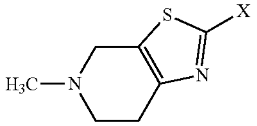

wherein X represents a halogen atom or a —O—S(O)$_2$—R$^0$ group (wherein R$^0$ represents an optionally substituted C1-C6 alkyl group or an optionally substituted phenyl group)

with the following compound (5) or a salt thereof:

(5)

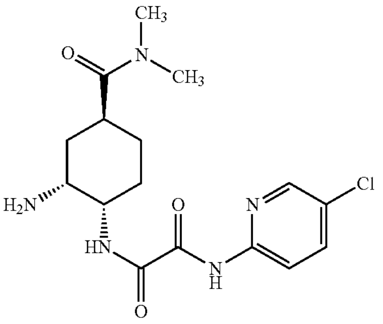

in the presence of a base and a palladium catalyst containing a phosphine ligand in a solvent under a carbon monoxide atmosphere to produce compound (X); and (b) treating compound (X) with p-toluenesulfonic acid monohydrate in aqueous ethanol to provide the p-toluenesulfonic acid monohydrate of compound (X) represented by formula (X-a):

(X-a)

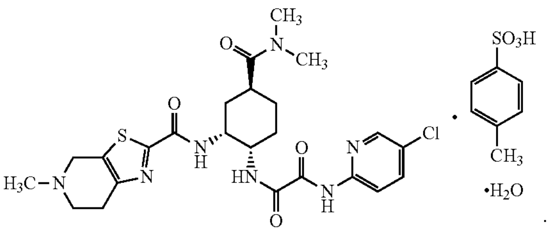

12. A method for producing a p-toluenesulfonic acid monohydrate of a compound represented by formula (X):

(X)

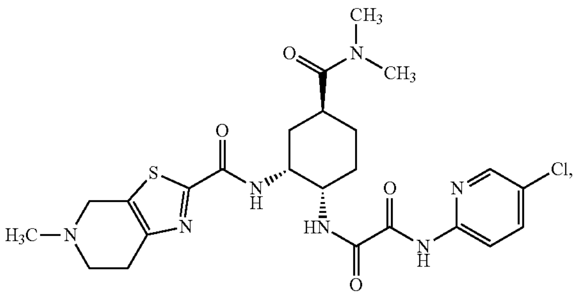

the method comprising:

(a) mixing a compound represented by formula (1-x), a salt thereof, or a hydrate of the compound or the salt:

(1-x)

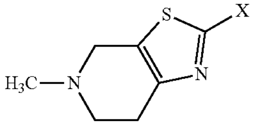

wherein X represents a halogen atom or a —O—S(O)$_2$—R$^0$ group (wherein R$^0$ represents an optionally substituted C1-C6 alkyl group or an optionally substituted phenyl group)

with any of the following:

(i) a compound represented by formula (3-b): R$^3$—OH (3-b) under a carbon monoxide atmosphere wherein R$^3$ represents a C1-C6 alkyl group or an optionally substituted phenyl group, in the presence of a base and palladium (II) acetate catalyst containing 4,5-bis(diphenylphosphino)-9,9-dimethylxanthene (xantphos) phosphine ligand in a solvent, wherein the catalyst is present in the amount 0.1-10 mol %;

or (ii) a compound represented by formula (4-b): R$^3$—O—CHO (4-b)

wherein R$^3$ represents an optionally substituted phenyl group in the presence of a base and a palladium (II) acetate_catalyst containing 4,5-bis(diphenylphosphino)-9,9-dimethylxanthene (xantphos) phosphine ligand in a solvent, wherein the catalyst is present in the amount of 0.1-10 mol, to produce a compound represented by formula (1-3) or a salt thereof:

(1-3)

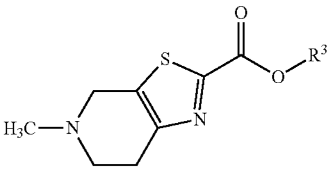

wherein R$^3$ represents a C1-C6 alkyl group or an optionally substituted phenyl group;

subsequently alkali-hydrolyzing the compound represented by formula (1-3) to produce compound (1-c) or a salt thereof:

(1-c)

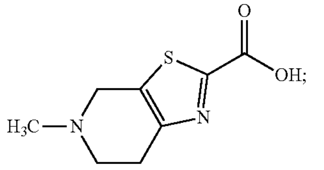

and subsequently mixing the compound represented by formula (1-c) with compound (5) or a salt thereof:

(5)

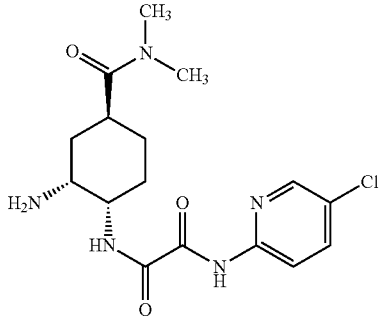

in the presence of a base and a condensing agent to produce compound (X), and (b) treating compound (X) with p-toluenesulfonic acid monohydrate in aqueous ethanol to provide the p-toluenesulfonic acid monohydrate of compound (X) represented by formula (X-a):

(X-a)

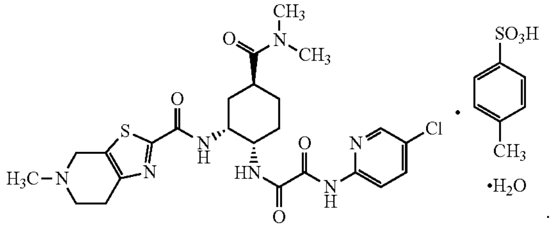

13. A method for producing a p-toluenesulfonic acid monohydrate of a compound represented by formula (X):

(X)

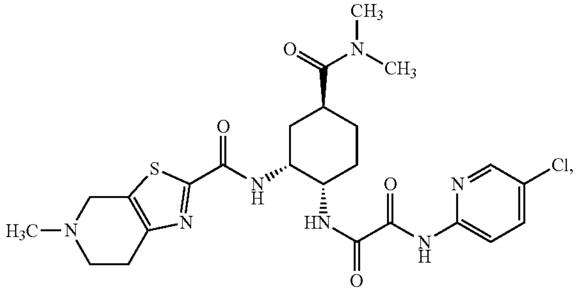

the method comprising:

(a) mixing a compound represented by formula (1-x), a salt thereof, or a hydrate of the compound or the salt:

(1-x)

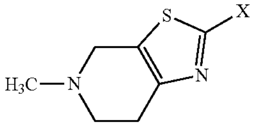

wherein X represents a halogen atom or a —O—$S(O)_2$—$R^0$ group (wherein $R^0$ represents an optionally substituted C1-C6 alkyl group or an optionally substituted phenyl group)

in the presence of a base, acetic anhydride, a formic acid derivative selected from potassium formate or sodium formate and a palladium catalyst containing a phosphine ligand in a solvent to produce compound (1-c) or a salt thereof:

(1-c)

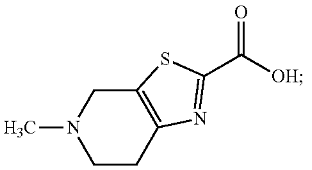

and subsequently mixing the compound (1-c) or the salt thereof with a compound represented by the following formula (5) or a salt thereof:

(5)

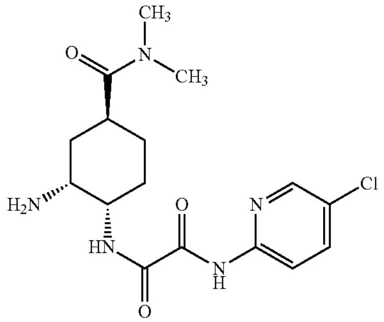

in the presence of a tertiary amine and a condensing agent to produce compound (X); and (b) treating compound (X) with p-toluenesulfonic acid monohydrate in aqueous ethanol to provide the p-toluenesulfonic acid monohydrate of compound (X) represented by formula (X-a):

(X-a)
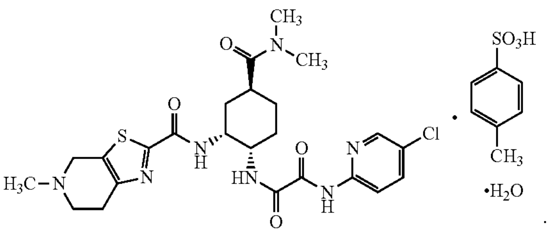
* * * * *